(12) United States Patent
Moon et al.

(10) Patent No.: US 11,642,671 B2
(45) Date of Patent: May 9, 2023

(54) ELECTROWETTING ON DIELECTRIC (EWOD) DEVICE TO PERFORM LIQUID-TO-LIQUID EXTRACTION (LLE) OF BIOMOLECULES AND SYSTEMS AND METHODS FOR USING THE EWOD DEVICE

(71) Applicant: Board of Regents, The University of Texas System, Austin, TX (US)

(72) Inventors: Hyejin Moon, Austin, TX (US); Shubhodeep Paul, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/850,242

(22) Filed: Jun. 27, 2022

(65) Prior Publication Data

US 2022/0347676 A1 Nov. 3, 2022

Related U.S. Application Data

(62) Division of application No. 16/743,858, filed on Jan. 15, 2020, now Pat. No. 11,413,613.

(60) Provisional application No. 62/792,664, filed on Jan. 15, 2019.

(51) Int. Cl.
*B01L 3/00* (2006.01)
*C07K 1/24* (2006.01)
*B01D 11/04* (2006.01)

(52) U.S. Cl.
CPC ...... *B01L 3/50273* (2013.01); *B01D 11/0496* (2013.01); *B01L 3/502784* (2013.01); *C07K 1/24* (2013.01); *B01L 2400/0427* (2013.01)

(58) Field of Classification Search
CPC .......... B01L 3/50273; B01L 3/502784; B01L 2400/0427; B01L 3/502715; B01L 2300/0816; B01L 2300/0867; B01L 3/502792; B01D 11/0496; B01D 11/0488; B01D 11/0492; C07K 1/24
See application file for complete search history.

(56) References Cited

U.S. PATENT DOCUMENTS

| | | | |
|---|---|---|---|
| 2008/0185339 A1* | 8/2008 | Delapierre | B01D 11/04 210/243 |
| 2009/0220948 A1 | 9/2009 | Oviso et al. | |
| 2011/0091989 A1 | 4/2011 | Sista et al. | |
| 2015/0253320 A1 | 9/2015 | Kamei et al. | |
| 2018/0275088 A1 | 9/2018 | Huff et al. | |
| 2019/0329258 A1 | 10/2019 | Kinney et al. | |

* cited by examiner

*Primary Examiner* — Jennifer Wecker
*Assistant Examiner* — Oyeleye Alexander Alabi
(74) *Attorney, Agent, or Firm* — Thomas | Horstemeyer, LLP

(57) ABSTRACT

A method and system for performing biomolecule extraction are provided that use liquid-to-liquid extraction (LLE) in combination with an electrowetting on dielectric (EWOD) device to provide a biomolecule extraction solution that has high extraction efficiency and that is less costly and easier to use than current state of the art methods and systems. The system and method are well suited for, but not limited to, extraction of DNA, RNA and protein molecules.

8 Claims, 35 Drawing Sheets

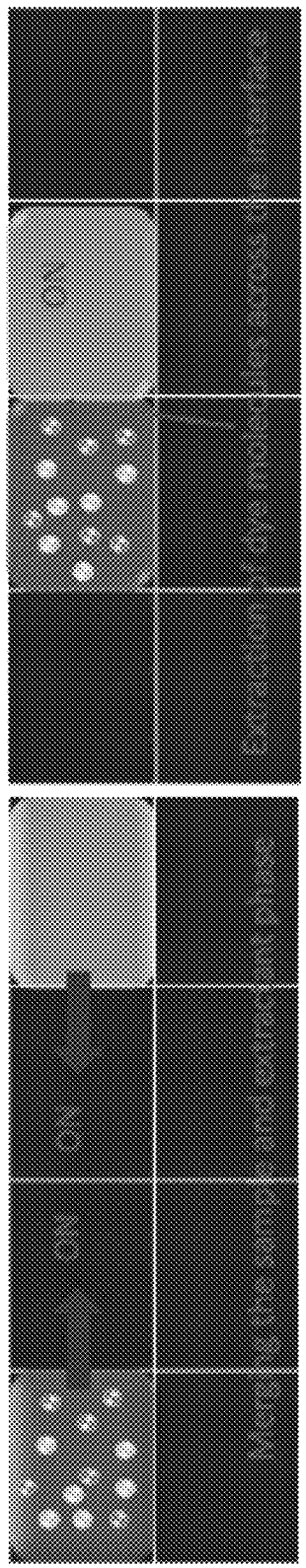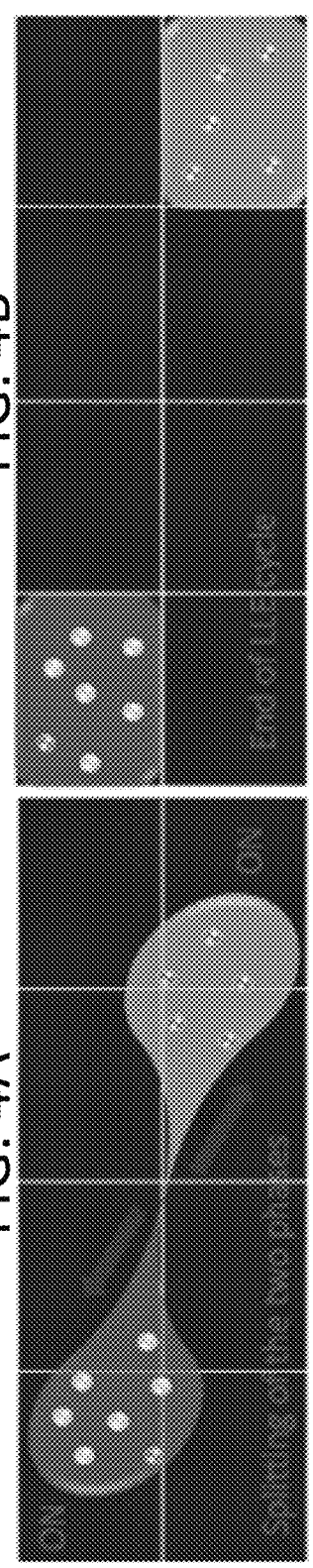

FIG. 13A  Moving the phases back and forth

FIG. 13B  Circular motion of the phases

FIG. 13C  Keeping one phase stationary while moving the other phase around.

ELECTROWETTING ON DIELECTRIC (EWOD) DEVICE TO PERFORM LIQUID-TO-LIQUID EXTRACTION (LLE) OF BIOMOLECULES AND SYSTEMS AND METHODS FOR USING THE EWOD DEVICE

CROSS-REFERENCE TO RELATED APPLICATIONS

This application is a divisional of co-pending U.S. utility application entitled "AN ELECTROWETTING ON DIELECTRIC (EWOD) DEVICE TO PERFORM LIQUID-TO-LIQUID EXTRACTION (LLE) OF BIOMOLECULES AND SYSTEMS AND METHODS FOR USING THE EWOD DEVICE," having Ser. No. 16/743,858, filed Jan. 15, 2020, which claims priority to, and the benefit of the filing date of, U.S. provisional application having Ser. No. 62/792,664, filed on Jan. 15, 2019, entitled "USING AN ELECTROWETTING ON DIELECTRIC (EWOD) DEVICE TO PERFORM LIQUID-TO-LIQUID EXTRACTION (LLE) OF BIOMOLECULES," each of which is hereby incorporated by reference herein in its entirety.

STATEMENT OF GOVERNMENT INTEREST

This invention was made with government support under Award No. 1254602 awarded by the National Science Foundation. The government has certain rights in this invention.

TECHNICAL FIELD OF THE INVENTION

The invention relates to biomolecule isolation. More particularly, the invention relates to systems and methods for using an electrowetting on dielectric (EWOD) device and liquid-to-liquid extraction (LLE) to isolate and extract biomolecules.

BACKGROUND OF THE INVENTION

With the continued investments in genomics-based precision medicines and diagnostics based on genetic variants, there is a need to make DNA isolation processes faster and less expensive. DNA isolation has traditionally been done using particle-based systems or membrane-based filtration processes. The current state of the art protocol for DNA isolation involves many steps (binding, washing, buffer exchange and elution) and the use of magnetic bead particles. The use of different buffers and magnetic particles adds to the cost of the process.

Several automated benchtop instruments have been commercialized that make use of the magnetic particle-based system for DNA isolation. These instruments are bulky and typically make use of robotic arms, many well plates, and many arrays of test tubes for multiple and consecutive separations. Commercial kits are available based on the membrane technology, but they are expensive, time consuming and require trained personnel. In addition, the isolation efficiency varies from kit to kit.

Although a growing number of published scientific reports call for alternative methods, such as LLE, for DNA isolation, such alternative methods have not been used on either macro scale automated instruments or on microfluidic device platforms to make the process simple and faster. Furthermore, it is difficult to control a two-phase LLE system in traditional macro scale instruments, which restricts the successful implementation of this process.

Nucleic acids, especially DNA, have emerged as one of the most important biomolecules for life science applications. With the developments in sequencing, PCR and other bioanalytical technologies, it is possible to answer a wide range of biological questions through genotyping and genomic profiling, which has paved the way for precision medicine. Sample preparation for these studies often involves cumbersome bench top procedures to extract the DNA, which must be of high purity. The most widely used method is solid phase extraction (SPE). FIG. 1 shows a magnetic bead-based SPE process for extracting DNA from other impurities (protein, RNA, etc.). The process involves many steps, as shown in FIG. 1, and the use of magnetic beads and various buffers, which add to the cost of the process.

This SPE method is regarded as the state of the art for isolating DNA from interfering protein and other cellular molecules. Commercially available kits and automated benchtop machines are available for extracting DNA from different cell lines and preparing the samples for downstream analysis. This SPE method of isolating DNA involves binding of the DNA molecules with solid (magnetic) particles that have specific affinity for the molecule. After capturing the molecules, the particles are washed to further remove the impurities and finally eluted to obtain the purified DNA sample, as shown in FIG. 1. Although this method has shown good success, the costs involved in this technique are high due in large part to magnetic beads typically being used as the solid phase particles.

Automated microfluidic approaches incorporating all the steps of SPE have been reported by several groups that purportedly reduce the cost and reagent consumptions and the footprint when compared to other automated machines. However, these automated microfluidic devices execute several of the above steps involved in SPE-based DNA isolation, including the binding, washing, buffer exchange and elution steps. They also typically use the magnetic bead particles.

Although a much simpler alternative process, LLE has not been explored very much for DNA isolation on a microfluidic device. LLE used for DNA isolation traditionally has been performed via phenol-chloroform system extraction, which suffers from the major drawback of phenol being toxic. Also, because phenol has high wavelength absorptivity at 260 nanometers (nm), it becomes difficult for the quantification of extracted DNA.

Ionic liquid (IL) has been proposed as an alternative sorbent for encapsulating DNA molecules with LLE. ILs, which are often referred to as green solvents with high thermal stability and low vapor pressure, are environmentally friendly. In addition, the easy tunability of the structures of ILs make them favorable extractants for DNA molecules. ILs have also been reported to be a good medium for DNA storage for longer durations at room temperature. Also, given by the low vapor pressure and thermal stability of ILs, downstream processes that require incubation at high temperature for longer periods can be achieved with IL as the medium. ILs have also been reported as medium compatible with PCR. Magnetic Ionic liquids (MIL) have also been reported for DNA extraction for sample preparation. They have been reported to have a high extraction efficiency, but in order to separate the phases at the end of LLE, an external magnetic field is used.

A need exists for a solution for extracting biomolecules that is efficient and less costly and easier to use than the aforementioned solutions.

BRIEF DESCRIPTION OF THE DRAWINGS

FIGS. 4A-4D show the mixing region 12 of an EWOD device during different stages of the LLE process in accordance with a representative embodiment.

DETAILED DESCRIPTION

Figure 1:
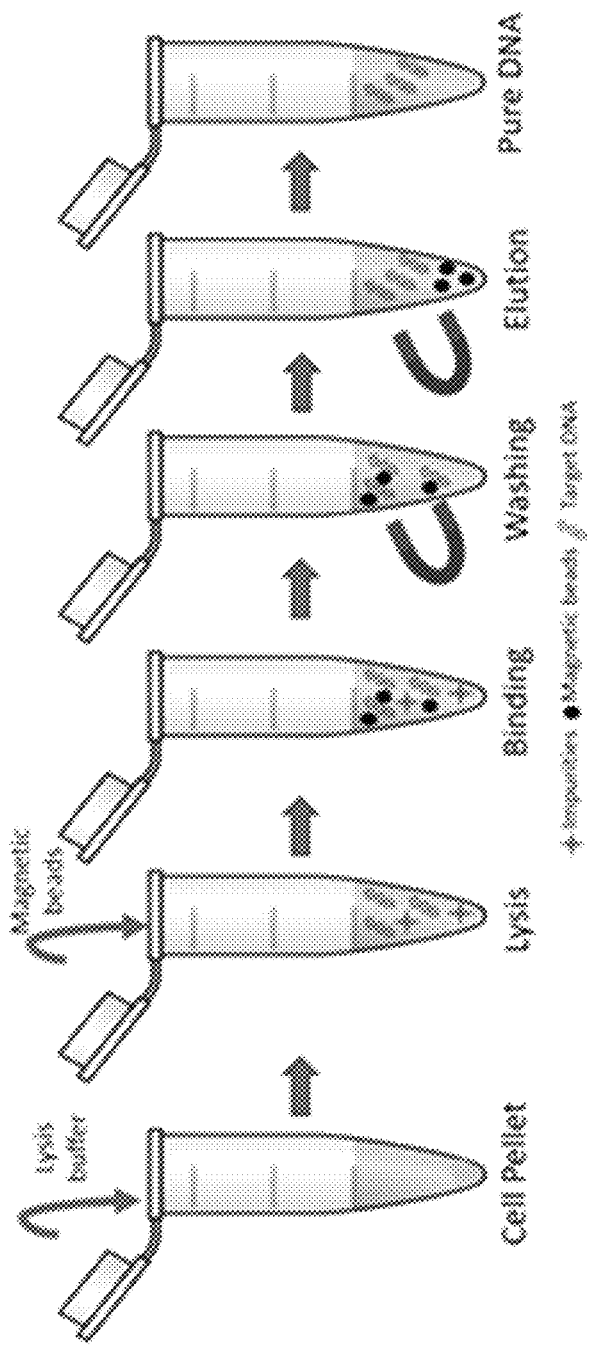
FIG. 1 shows a magnetic bead-based SPE process traditionally used for extracting DNA from other impurities (protein, RNA, etc.).

In accordance with representative embodiments, a method and system for performing biomolecule extraction are provided that use LLE in combination with an EWOD device to provide a biomolecule extraction solution that has high extraction efficiency and that is less costly and easier to use than current state of the art methods and systems.

In the following detailed description, for purposes of explanation and not limitation, example embodiments disclosing specific details are set forth in order to provide a thorough understanding of an embodiment according to the present teachings. However, it will be apparent to one having ordinary skill in the art having the benefit of the present disclosure that other embodiments according to the present teachings that depart from the specific details disclosed herein remain within the scope of the appended claims. Moreover, descriptions of well-known apparatuses and methods may be omitted so as to not obscure the description of the example embodiments. Such methods and apparatuses are clearly within the scope of the present teachings.

The terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms "a," "an," and "the" include both singular and plural referents, unless the context clearly dictates otherwise. Thus, for example, "a device" includes one device and plural devices.

Relative terms may be used to describe the various elements' relationships to one another, as illustrated in the accompanying drawings. These relative terms are intended to encompass different orientations of the device and/or elements in addition to the orientation depicted in the drawings.

It will be understood that when an element is referred to as being "connected to" or "coupled to" or "electrically coupled to" another element, it can be directly connected or coupled, or intervening elements may be present.

Exemplary, or representative, embodiments will now be described with reference to the figures, in which like reference numerals represent like components, elements or features. It should be noted that features, elements or components in the figures are not intended to be drawn to scale, emphasis being placed instead on demonstrating inventive principles and concepts.

In accordance with a preferred embodiment, the system comprises a digital microfluidic platform that has the capability of handling a multi (e.g., two) phase liquid system and of controlling the interface of the liquid phases, which is difficult in known macro and microfluidic platforms. The digital microfluidic platform can perform LLE-based DNA isolation successfully, which drastically reduces the sample consumption and allows the entire process to be automated and hands free. Similar digital microfluidic platforms have been used in the past for diagnostics, PCR, genomics, sequencing and genetic engineering studies, but those platforms are magnetic particle-based platforms, and therefore have the aforementioned disadvantages associated with magnetic particle-based systems. Furthermore, for those applications, the primary step is to have a sample enriched with the target molecule (DNA), which nowadays is conducted using macro scale bulky instruments or kits.

In accordance with a representative embodiment, the biomolecule (e.g., DNA) sample preparation and isolation steps can both be performed on the microfluidic platform. Alternatively, the system can be used as a standalone isolation device with the other downstream process done in other facilities, which provides an arena for possible replacement of macro scale DNA isolation instruments and kits.

While the representative embodiments are described herein with reference to DNA extraction, the method and system described herein can be used for isolating other biomolecules, protein and RNA for their analysis. Recently, there has been great interest in single cell multi-omics research and process development, which involves isolating DNA, RNA and protein molecules from a single cell for their profiling. The microfluidic platform disclosed herein can also be used for such isolation and encapsulation of each type of the biomolecules in separate droplets for their respective downstream profiling.

Figure 2:
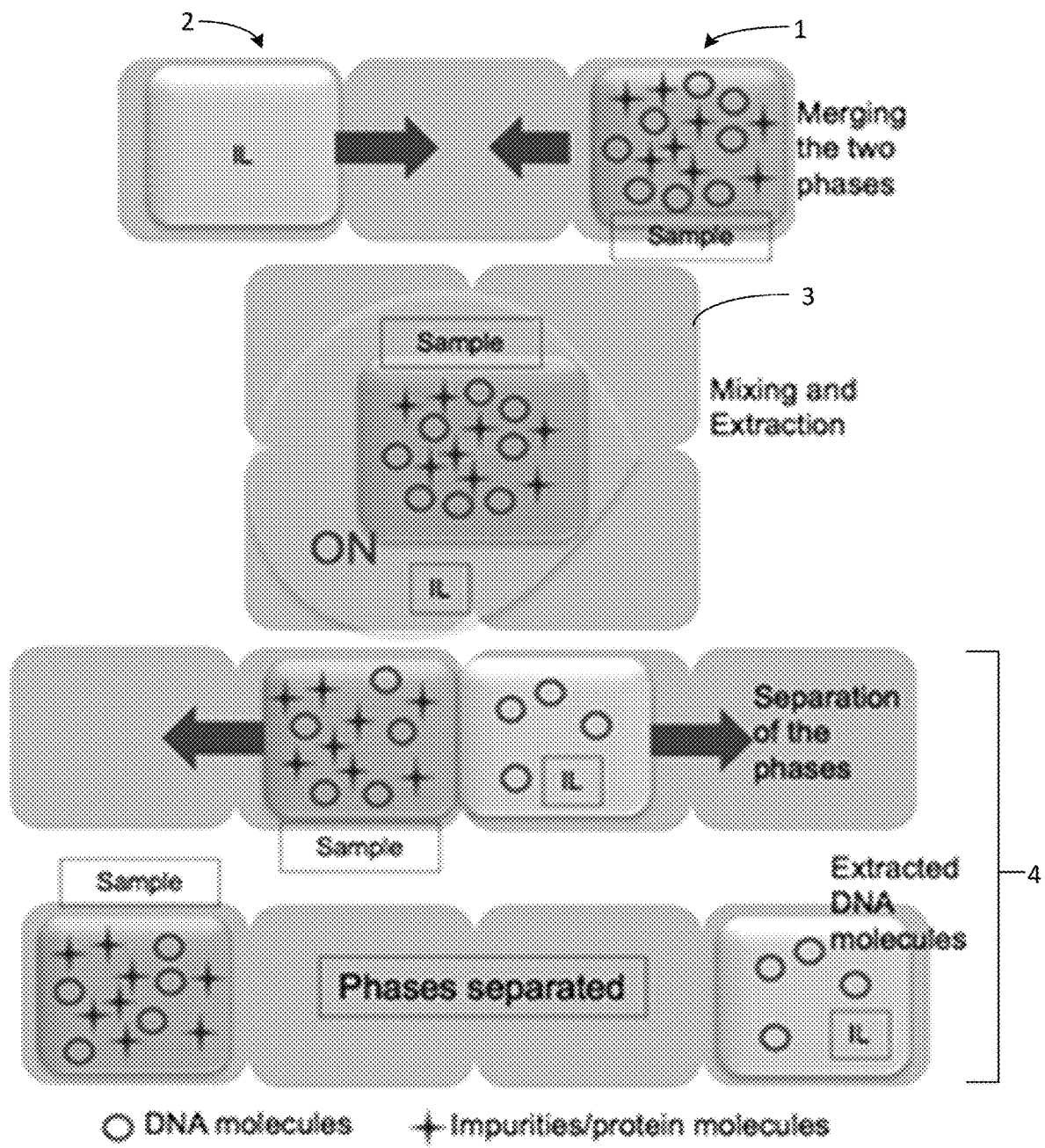
FIG. 2 is a process flow diagram illustrating the drop to drop DNA LLE format in accordance with a representative embodiment.

FIG. 2 is a process flow diagram illustrating the drop-to-drop (DTD) DNA LLE format of the DNA LLE method performed by an EWOD device (not shown) in accordance with a representative embodiment. The DNA diffuse into the IL phase through the interface formed by the two immiscible fluids. A liquid one droplet 1, which is the sample phase droplet, and a liquid two droplet 2 that will act in this case as the extractant, are introduced into the EWOD device, which is described below in more detail with reference to FIG. 5. During a mixing and extraction process 3 in the EWOD device, the liquid one and liquid two droplets are mixed together in a predetermined manner that is described below in more detail. During mixing, the target biomolecules, which in this case are DNA molecules, are extracted from the liquid one droplet into the liquid two droplet. In a separation process 4 in the EWOD device, the liquid one droplet and the liquid two droplet are separated, with the extracted DNA molecules remaining in the liquid 2 droplet.

In the following discussion, three separate studies are disclosed that describe various representative embodiments for performing the method shown in FIG. 2. The first study is focused on the demonstration of a representative embodiment of the LLE protocol in a DTD format on EWOD digital microfluidics (DMF) devices. The study was done to show the separation of color dye analytes in a binary solution mixture using an EWOD platform. Absorbance-based concentration measurement was miniaturized and integrated with the platform to evaluate the performance of the on-chip LLE protocol. The study demonstrated the capability of EWOD-based LLE to separate molecules in a sample.

The second and the third studies are focused on extending the capability of EWOD DTD LLE for the separation of DNA molecules from other impurities in the sample. Plasmid DNA was used as the model DNA, and bovine serum albumin (BSA) protein molecules were used as impurities to show the capability of EWOD LLE to isolate the DNA molecules selectively. Different liquid-liquid systems were studied for the on-chip DNA extraction other than the traditional phenol extraction method. The second study is focused on the LLE of DNA using ionic liquid (IL) as an extractant. Hydrophobic IL, which forms a two-phase system with the aqueous sample, is an excellent solvent for DNA isolation. The capability of EWOD devices to isolate DNA molecules using aqueous/IL (Aq./IL) is highlighted in the second study. The third study is focused on the integration of aqueous two-phase systems (ATPS) for DNA extraction on the EWOD device. EWOD has already shown the capability to handle ATPSs, and this last study was done to demonstrate the integration of a aqueous two-phase extraction (ATPE) process for isolating DNA molecules on EWOD devices for the first time. It was observed that by changing the liquid-liquid systems, there were significant changes in the final extraction yield from the on-chip LLE process.

First Study

Experimental Setup
 Working Fluids
  To demonstrate the separation of a binary solution on EWOD DMF by LLE, two organic dyes were selected as the solutes, namely, acid green 25 ($C_{28}H_{20}N_2Na_2O_8S_2$) and reactive yellow 17 ($C_{20}H_{20}K_2N_4O_{12}S_3$) (provided by Organic Dyestuffs Corporation). The sample phase was prepared by mixing equal amounts of these two dyes. The final concentration of each analyte in the sample mixture formed was 1250 µg/ml for all the EWOD LLE experiments.

Water-immiscible IL (1-butyl-3-methylimidazolium hexafluorophosphate (BMIM-PF6) was used as the other phase, which is referred to herein as the extractant phase. The IL was purchased from Sigma Aldrich. ILs have been previously reported in several studies as an extractant for different molecules, including DNA. Some of the other properties of IL, such as negligible evaporation, high thermal stabilities, compatible medium for biomolecules, and tunable chemical and physical properties make it a suitable medium for downstream processing of the extracted material.

The other properties of BMIM-PF6 is a viscous, colorless, hydrophobic, and non-water-soluble ionic liquid with a melting point of −8° C. Together with 1-butyl-3-methylimidazolium tetrafluoroborate, BMIM-PF6, it is one of the most widely studied ILs. It is known to decompose very slowly in the presence of water. The chemical structure comprises BMIM cation and PF6 anion.

Device Design, Fabrication and Operating Conditions

A standard parallel plate EWOD DMF device was utilized. Briefly, each device was assembled using an ITO coated glass substrate on top. After dispensing the sample and extractant phase into the reservoirs, the top plate was assembled. A spacer of 100 micrometer (μm) was maintained to separate the top and bottom plates from each other. A 100 to 110 volt (V) at 1 kilohertz (kHz) electromagnetic field was used to facilitate the droplet movement. A Hirox™ camera was used for visualization and documentation of the procedure.

For the LLE process on an EWOD DMF electrode array, the droplets were generated, mixed, and split during the process. The integrated real-time concentration measurement system included two light emitting diode (LED) light sources and a photodiode for the measurement of light intensity passing through the sample. The light intensity was converted to voltage measurements, the values of which were used to obtain the sample concentration after the LLE process. The on-chip concentration method quantified the yield of the LLE process. The detailed description of the steps of on-chip concentration is described below in more detail.

Drop-to-Drop LLE Process on EWOD

Figure 3A:
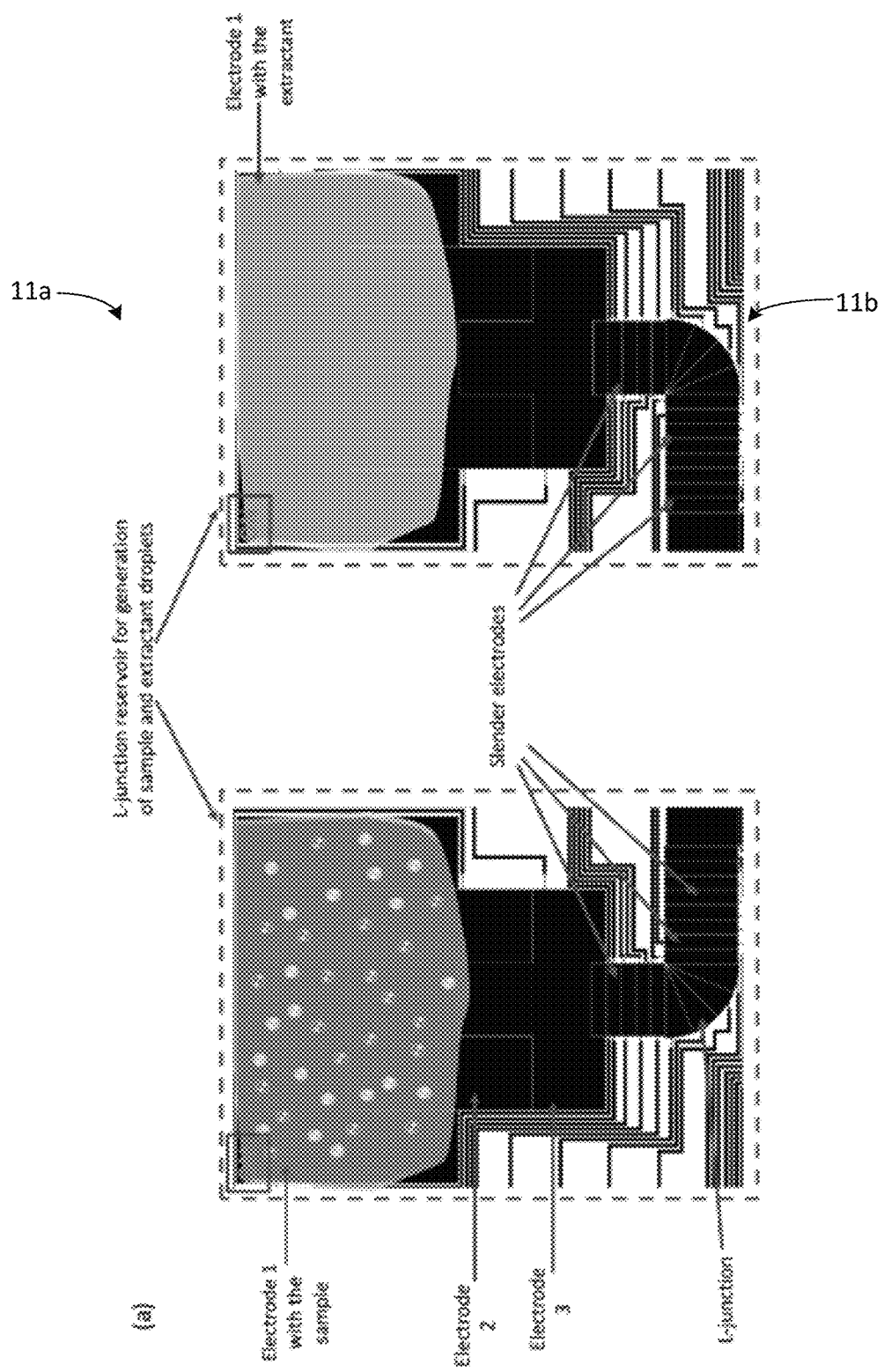
FIGS. 3A-3C are partial views of a portion of an EOWD device in accordance with a representative embodiment that includes first and second L-junction reservoirs and a plurality of electrodes.
Figure 3B:
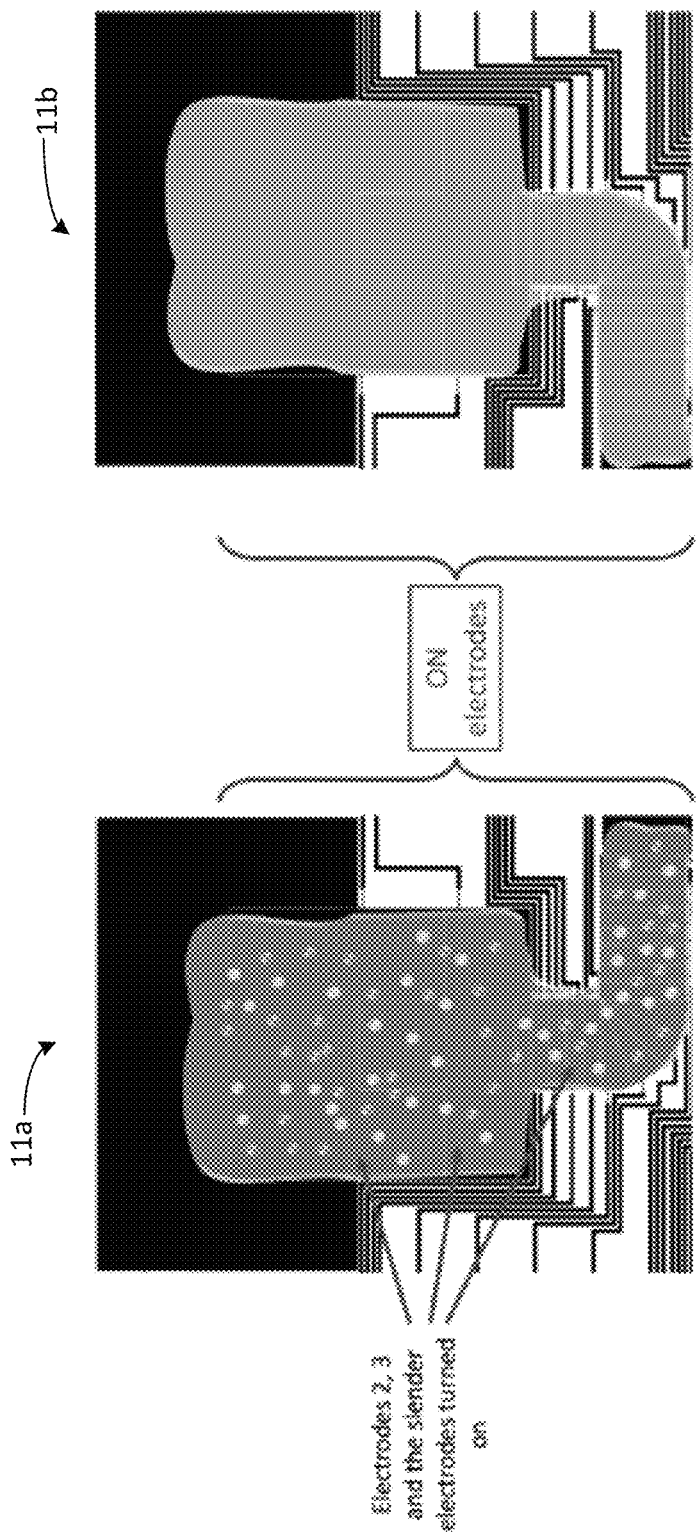
Figure 3C:
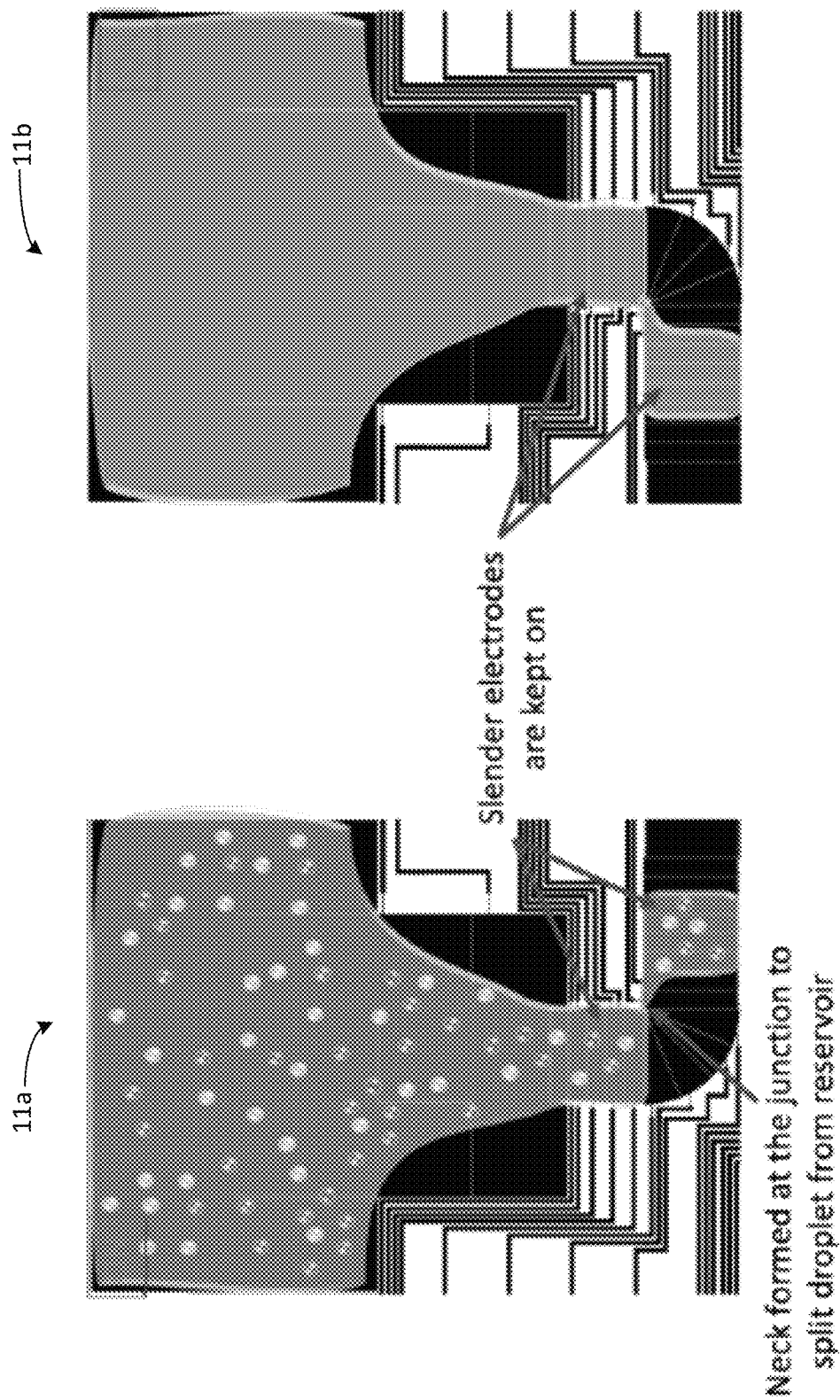

FIGS. 3A-3C are partial views of a portion of the EOWD device in accordance with a representative embodiment that includes first and second L-junction reservoirs 11a and 11b and a plurality of electrodes, labeled "electrode 1," "electrode 2," "electrode 3" and "slender electrodes." Droplet generation: The sample and the IL phase droplets (extractant) were generated from the two different L-junction reservoirs 11a and 11b, respectively, which can generate equal volumes of droplets fabricated in the LLE device. FIGS. 3A-3C show the entire process of droplets generations for the LLE study.

The fluids are initially introduced on the electrode marked as electrode 1, as shown in FIG. 3A. In the first step of droplet generation, the entire liquid volume is pulled to fill the slender electrodes, as shown in FIG. 3B, by turning them on and turning off electrode 1. Next, the electrodes 2, 3, and the slender electrodes are turned off, and electrode 1 is switched back on. Consequently, the electrowetting forces create a neck at the junction between the activated electrodes, and the liquid instability at the neck finally forms a droplet, as shown in FIG. 3C. After generation, the droplets were moved to the mixing region of the EWOD device where the LLE takes place, as will now be described with reference to FIGS. 4A-4D.

FIGS. 4A-4D show the mixing region 12 of the EWOD device during different stages of the LLE process in accordance with a representative embodiment. The arrows in FIGS. 4A-4D show the directions of the droplets. FIG. 4A depicts the sample droplet containing the solutes (green and yellow dye molecules) and the IL droplet being driven toward one another to cause the droplets to merge. FIG. 4B depicts mixing of the merged droplets to fasten the extraction, and the solutes diffusing from sample to the extractant. FIG. 4C depicts splitting of the two phases once the extraction is completed. FIG. 4D depicts the sample (without green solute) and the extractant (with green solute) after the successful phase splitting.

In FIG. 4A, the dispensed droplets are further actuated along the electrode paths simply by activating the consecutive square electrodes one after the other. In FIG. 4B, merging sample and extractant droplets is accomplished by bringing the two droplets onto to adjacent electrodes. In FIG. 4C, the merged sample and extractant droplets are mixed by systematically activating electrodes. Separate experiments were conducted to study the effects of different mixing schemes on the LLE yield. In FIG. 4D, once the extraction is completed, phase splitting is also accomplished by driving the two phases onto two separate opposite electrodes. The splitting of the phases marks the completion of one cycle of the LLE process.

The extraction can be observed in real-time through the digital microscope. Spectrophotometry was integrated into the system to measure real-time concentration change at the end of the LLE process. After obtaining linear calibration curves on-chip for each of the analytes, this method of quantification was adopted. Details of the method are described in section 4.2.5.

Off-Chip LLE and Dye Characterization

Off-chip LLE experiments were conducted in Eppendorf tubes for each of the dyes separately. Their extraction yield for the liquid-liquid system was studied. Separate green and yellow dye samples with a concentration of 1 mg/ml were used. An equal volume of the sample and IL were introduced in the tube and vortexed for a few minutes for proper mixing. At the end of the LLE, phases were split, and samples were transferred to a plate-based spectrophotometer for concentration measurement.

Wavelengths at which absorbance is maximum for each analyte were obtained by sweeping over a range in a plate-based spectrophotometer. The wavelength of maximum absorptivity was found to be 650 nm for green dye and that of 430 nm for the yellow dye. These wavelengths were used for all the on-chip and off-chip absorbance measurements.

On-Chip Concentration Measurement

Figure 5:
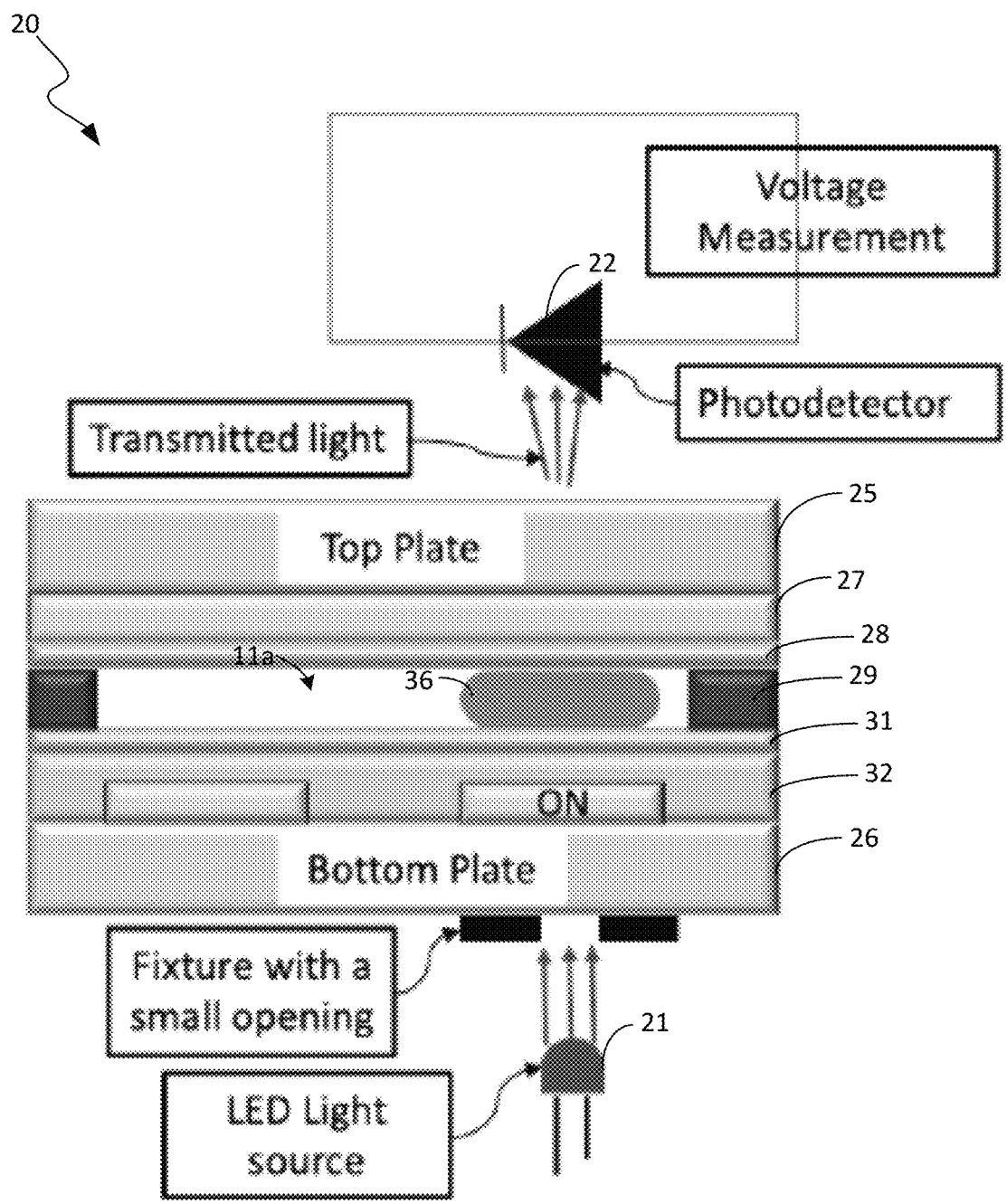
FIG. 5 is a block diagram of the EWOD device in accordance with a representative embodiment.

FIG. 5 is a block diagram of the EWOD device 20 in accordance with a representative embodiment used in the experimental setup. The EWOD device may have many different configurations, and the inventive principles and concepts are not limited to the representative embodiment shown in FIG. 5, as will be understood by those of skill in the art. On-chip concentration measurement was done by the absorbance method to quantify the change in the concentration of individual analytes in the sample. Two LEDs with 650 nm and 430 nm dominant wavelengths were used as the light source. Only one of the LEDs 21 is visible in the block diagram shown in FIG. 5. The LEDs 21 were housed in three-dimensional (3-D) printed boxes (not shown) with openings smaller than the droplet size so that not much of the light was dispersed in other directions. A photodiode 22 was used to measure the voltage, corresponding to the sample concentration of each dye in the sample.

For the sandwiched drop configuration type of EWOD device shown in FIG. 5, the device design mainly involved the design of the bottom plate 26. The arrangement of electrodes should be designed by considering the desired droplet actuation patterns. Software tools, such as the LayoutEditor software tool, for example, can be used to design the electrode patterns. Unless for complicated devices that need separate elements, such as sensors, typically, the top electrode completely covers the top plate 25 and does not need any designing.

For the experimental setup, the bottom plate 26 was fabricated on a circular wafer. The bottom plate 26 generally comprises (i) electrodes, which are separated by a small gap (~10 μm), (ii) contact pads, which facilitate the electrical connection between electrodes and the voltage supply, and (iii) contact lines that connect electrodes with their corresponding electrode pads. The electrode pads are powered to provide a voltage across each electrode (turn electrode ON). The voltage supply may be applied through external switches, each of which corresponds to one electrode on the bottom plate 26 of the EWOD device 20. For the experimental setup, signals to the switches, with the information whether the corresponding electrode should be on or off, are sent by a custom-built Lab View program as per the user request. How the EWOD device 20 may be assembled and operated is discussed below in more detail.

The mask design used for manufacturing the EWOD device 20 in accordance with a representative embodiment has a combination of i) L-junction reservoirs 11a and 11b (FIGS. 3A-3C) for equal volume droplet generation, and ii) typical square electrodes for the rest of the LLE protocol (mixing and splitting phases). The L shape was created by thin strips of electrodes, which are the slender electrodes in FIGS. 3A-3C. L-junction reservoirs were selected because they are capable of generating an equal volume of droplets continuously and consistently, as is known in the art.

The top and bottom plates 25 and 26, respectively, were fabricated in a cleanroom having micro/nanofabrication facilities. The bottom plate 26 fabrication was performed using standard photolithography and wet etching processes. An Indium tin oxide (ITO) layer 27 obtained from Delta technologies Ltd. of Stillwater, Minn. coated a glass substrate was used as the top and bottom plates 25 and 26, respectively.

The process of manufacturing the top and bottom plates 25 and 26, respectively, starts with cleaning the wafer thoroughly with non-halogenated hydrocarbons: acetone, methanol, isopropanol, and then rinsing with deionized (DI) water. The wafer is then dehydrated at 150° C. for 5 minutes. For the bottom plate 26, at first, a chemical hexamethyldisilazane (HMDS) is coated on the wafer with a spin coater. The following recipe for spin coating was used: spin speed of 500 rpm with a ramping rate of 100 rpm/s for 5 s; ramping with 900 rpm/s to 4000 rpm for 30 s. The thin HMDS layer provides excellent adhesion between the ITO layer 27 and the photoresist (PR), which will be deposited next. After the coating of the HMDS layer, the wafer is baked at 150° C. for 3 minutes.

Next, a positive resist (PR) (Microchem S1813) is spin-coated on the wafer with the following recipe: spin speed of 500 rpm with a ramping rate of 100 rpm/s for 5 s; ramping with 900 rpm/s to 3000 rpm for 30 s. The spin coat results in a uniform 1.2 μm thick PR layer. The glass substrate with the coated PR layer is then baked at 120° C. for 2 minutes. Next, the mask and the wafer are aligned using a backside aligner (OAI 806MBA). Particular areas of the PR layer are exposed to UV light with a light dose of 140 mJ/cm$^6$ for 7.5 s, and the rest is protected with the mask. The UV exposure step is followed by baking the wafer at 115° C. for 1 minute 30 s.

After the UV exposure, the wafer is dipped in a developer solution (Microchem, MF-319) and rinsed with DI water and dehydrated. The PR layer takes up the shape of the mask, with the exposed areas being washed away. The resulted PR pattern is checked under the microscope for accuracy. The wafer is then dipped in a mixture of Hydrochloric (HCL) acid, Nitric (HNO3) acid and DI water (H2O) (wt. %-20% HCl, 5% HNO3, 75% H2O or vol %-8:1:15, HCl:HNO3:H2O) for 2.5 minutes at 55° C. to etch the ITO layer in the areas where the PR does not cover it. At the end of the etching process, the PR is removed by dipping the wafer in a PR stripper solution (PR Remover 1165, Microchem). After removing the PR layer, the wafer is dehydrated at 150° C. for 5 minutes.

Next, to provide an insulation layer, a dielectric material (SU-8-5, Microchem) 32 is spin-coated on the wafer with the following recipe; the spin speed of 500 rpm with a ramping rate of 100 rpm/s for 5 s; spin speed 2000 rpm with a ramping rate of 900 rpm/s for 30 s. The spin coat results in a 5 μm thick uniform dielectric layer. The wafer is next baked to harden the layer at 65° C. for 1 minute, followed by a second baking step at 95° C. for 3 minutes. For further hardening the dielectric layer 32, it is then exposed to UV light with a light dose of 140 mJ/cm$^6$ for 9 s. The wafer is then baked at three temperatures: 65° C. for 1 minute, 95° C. for 1 minute, and 150° C. for 5 minutes. A hydrophobic layer 28, 31 is next created by spin coating a 300 nm thick uniform Teflon layer with the following recipe: spin speed of 1000 rpm with a ramping rate of 300 rpm/s for 30 s. For the top chip, an ITO coated wafer is first cleaned thoroughly with non-halogenated hydrocarbons: acetone, methanol, isopropanol, and then rinsed with DI water. It is then dehydrated at 150° C. for 5 minutes. A 300 nm thick Teflon layer is deposited using the same recipe described before.

Figure 6:
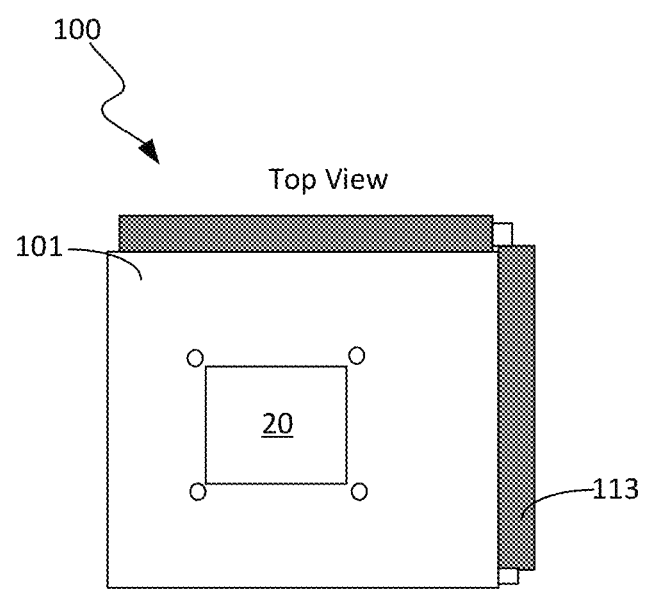
FIGS. 6 and 7 show top and bottom views, respectively, of a device assembly, or system, comprising the EWOD device shown in FIG. 5 in accordance with a representative embodiment.
Figure 7:
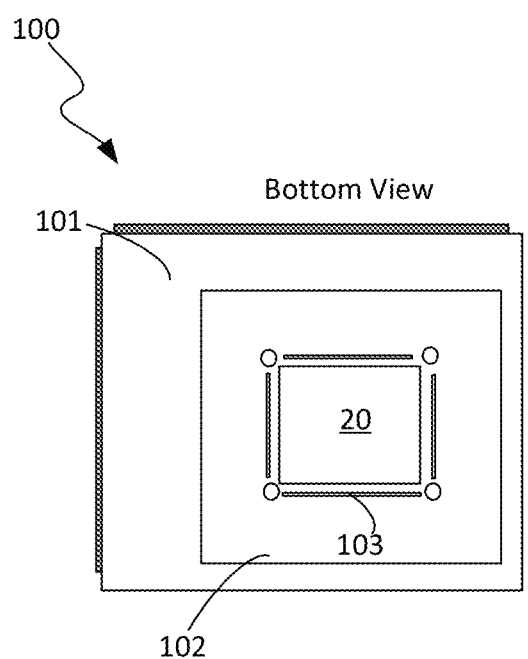

FIGS. 6 and 7 show top and bottom views, respectively, of the complete device assembly, or system, 100 comprising the EWOD device 20 shown in FIG. 5 in accordance with a representative embodiment. The system 100 comprises a printed circuit board (PCB) 101, a plexiglass holder 102, the EWOD top and bottom plates 25 and 26, respectively, four z-directional conducting strips 103. The EWOD bottom plate is attached to the plexiglass holder 102 using tape. Small strips of Kapton tape (DuPont™ Kapton® HN polyimide film) 29 (FIG. 5) are attached to the bottom chip 26, 32, 31 to create the gap with the top chip 25, 27, 28 that forms the reservoirs. To accommodate the z-directional conducting strips 103, the plexiglass holder 102 has via holes to hold them and make the connection between the switches on the PCB 101 and the contact pads located on the bottom chip 26, 32, 31. Before doing the experiments, the reservoir 11a is filled with the desired liquid 36, and the top chip 25, 27, 28 is placed on the Kapton tape strips 29, thereby sandwiching the liquid 36 between the top and bottom plates 25 and 26, respectively. Finally, the system 100 is connected to the switching circuit via data cables.

Figure 8:
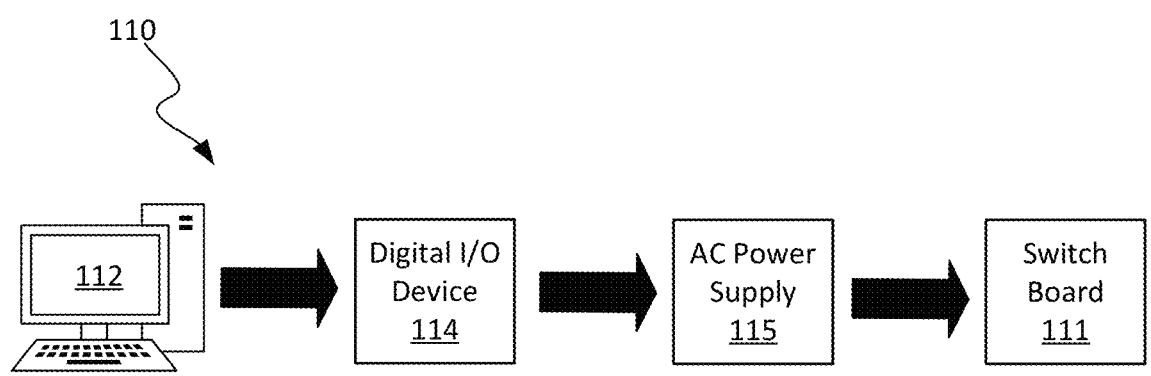
FIG. 8 shows a control system in accordance with a representative embodiment for controlling the system shown in FIGS. 6 and 7.

FIG. 8 shows a control system 110 in accordance with a representative embodiment for controlling the system 100 shown in FIGS. 6 and 7. Firstly, the system 100 shown in FIGS. 6 and 7 is connected to the switchboard 111. The control system 110 was used in the experimental setup, but control systems having many other configurations may be used to control the system, and may even be partially or wholly integrated onto the PCB 101 (FIGS. 6 and 7). Through a customized LABVIEW program running in a computer 112, instructions for switching the electrodes of the EWOD device 20 are sent to the switches of the switchboard 111, which is interfaced with the system 100 via a 50-pin ribbon connector 113 (FIG. 6). Voltage 5V or 0V is supplied to each switch when the signal for switching on or off is sent from the computer 112 through a digital Input/Output device and I/O connector 114. Electrodes of the EWOD device 20 corresponding to a particular switch will be activated or deactivated according to on or off status of switches. An alternating current (AC) power source and voltage amplifier 115 are used to amplify the supplied potential. A multimeter is used to monitor the applied voltage continuously.

With reference again to FIG. 5, the voltage generated by the photodiode 22 is directly proportional to the intensity of the light incident on the photodiode 22 passing through the sample 36. The absorbance by the analyte can be calculated from the measured voltage by the following equation:

$$A = \ln\left(\frac{V_0}{V}\right) \quad (1.1)$$

where, $V_0$ refers to voltage generated when the sample concentration is zero and V refers to the voltage generated at a certain concentration. Absorbance is also given by the Beer Lambert's law, $$A = \varepsilon \cdot l \cdot C \quad (1.2)$$

where, $\varepsilon$ is the extinction coefficient, l is the optical path length and C is the concentration of an analyte in the solution.

The system 100 was first calibrated for the two dyes separately to get a linear plot between absorbance and concentration. Stock solutions of separate green and yellow dye were made and serially diluted to obtain several standards. The starting concentration was 1230 µg/ml and was serially diluted to 156.25 µg/ml. Different standards of dye solutions were introduced into the EWOD device, and voltage was recorded from the light passing through the droplet and incident on the detector. For each concentration, the samples were exposed to the two LED light sources. Equation 1.1 was used to find the absorbance values for different concentrations of the green and the yellow dye solutions and calibration curves were plotted.

When working with a mixture of two components in a sample, both the components have a contribution to the absorbance value, and thus the absorbance is given by a new modified form of equation 1.2:

$$A = \varepsilon \cdot l \cdot C_g + \varepsilon \cdot l \cdot C_y \quad (1.3)$$

where, $C_g$ corresponds to concentration of the green dye and $C_y$ corresponds to the concentration of the yellow dye. Thus, for two wavelengths of light the following system of equations can be solved to find the concentration of each analyte.

$$A_1 = \varepsilon_g^1 \cdot l \cdot C_g + \varepsilon_y^1 \cdot l \cdot C_y \text{ (at } \lambda_1 = 430 \text{ nm)}$$

$$A_2 = \varepsilon_g^2 \cdot l \cdot C_g + \varepsilon_y^2 \cdot l \cdot C_y \text{ (at } \lambda_2 = 650 \text{ nm)} \quad (1.4)$$

where $\varepsilon_A^X$ is the coefficient of extinction for a solute A at wavelength X, l is the length of the path the light is travelling, and $\lambda_1$ and $\lambda_2$ are two different wavelengths, selected to have the greatest differences in absorbance between the two dyes.

The values of $\varepsilon_g^1 \cdot l$, $\varepsilon_g^2 \cdot l$, $\varepsilon_y^1 \cdot l$ and $\varepsilon_y^2 \cdot l$ obtained from the absorbance vs. concentration calibration curve for different concentration of each analyte over the two light sources. The slopes of the respective curves give us the $\varepsilon_A^X \cdot l$ values. The absorbance values at each wavelength due to the binary solution can be calculated by using Equation (1.1), with the measured voltage reading. With these known values, the system of linear equations (1.4) can be solved to find the individual dye concentration in the mixture.

Results and Discussions

Off-Chip LLE and Partition Coefficient of Analytes

Figure 9:
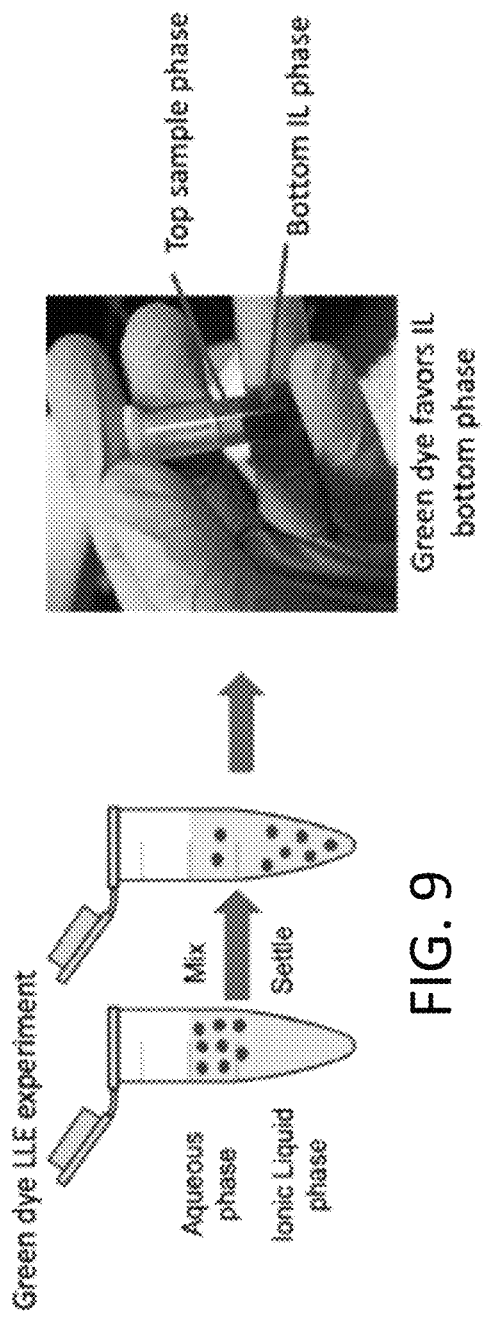
FIG. 9 is a diagram illustrating an off-chip LLE experiment with green dye that was conducted as part of one of the studies disclosed in the present disclosure.
Figure 10:
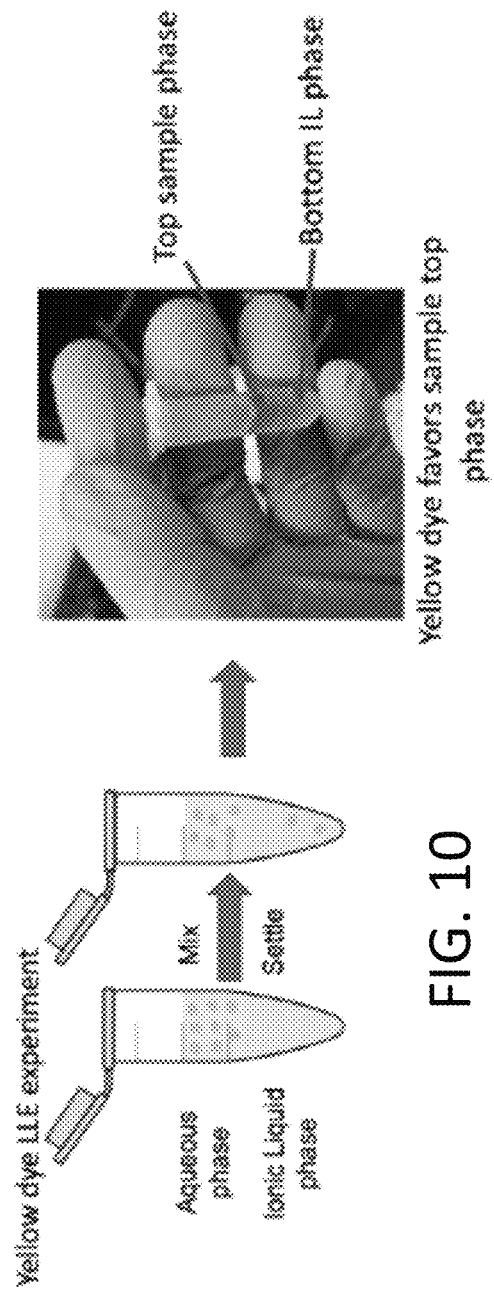
FIG. 10 is a diagram illustrating an off-chip LLE experiment with yellow dye that was conducted as part of one of the studies disclosed in the present disclosure

Off-chip LLE experiments were conducted as described above and illustrated in FIGS. 9 and 10. It can be observed visually from the off-chip LLE experiments that the green dye (FIG. 9) has a higher extraction yield compared to yellow dye (FIG. 10).

Figure 11:
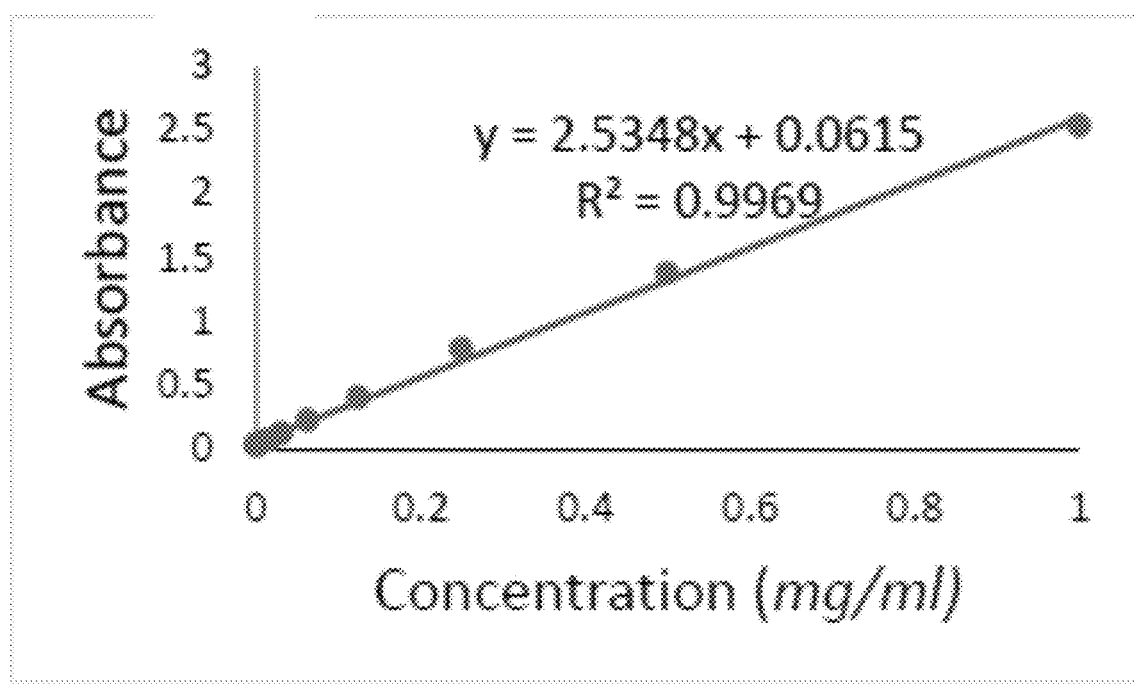
FIG. 11 shows a graph of a standardized curve for the green dye sample obtained at its wavelength of maximum absorbance for concentration measurement of the off-chip LLE experiment shown in FIG. 10.
Figure 12:
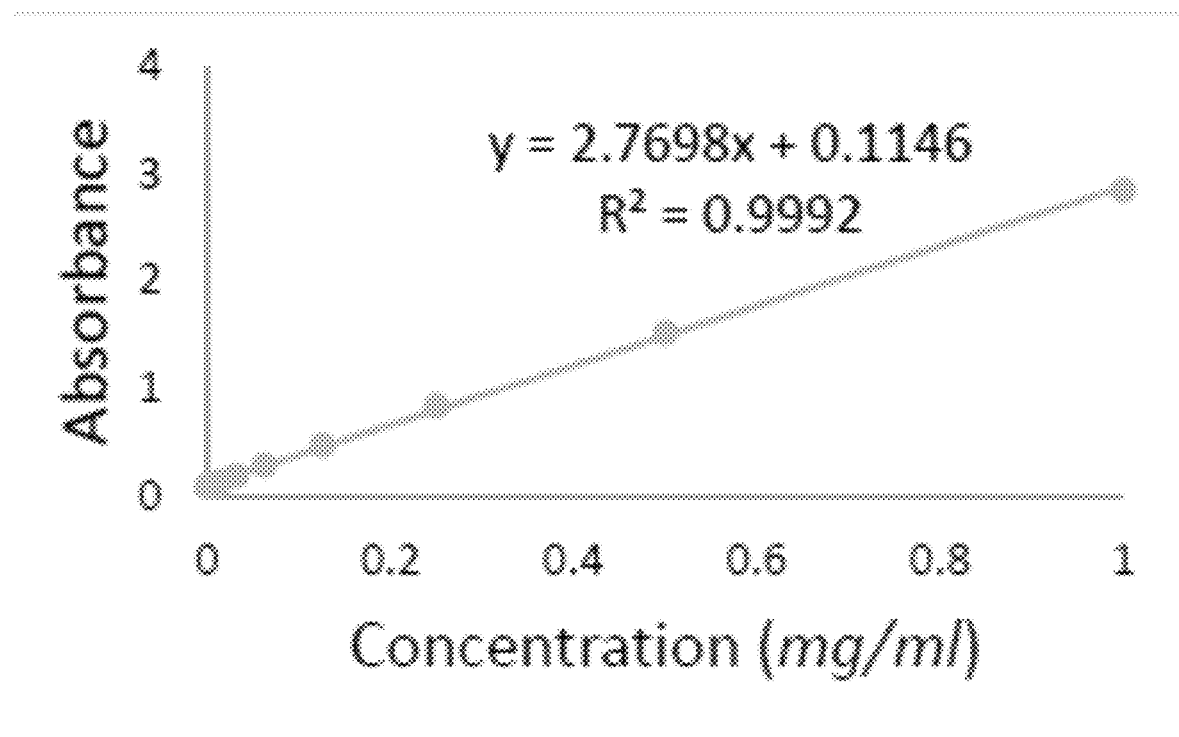
FIG. 12 shows a graph of a standardized curve for the yellow dye sample obtained at its wavelength of maximum absorbance for concentration measurement of the off-chip LLE experiment shown in FIG. 10.

FIGS. 11 and 12 show graphs of standardized curves for the green and yellow dye samples, respectively, obtained separately at their respective wavelengths of maximum absorbance for concentration measurement of the off-chip LLE experiments. Standards were prepared by serial dilution of the original stock solution of 1 mg/ml and were loaded into the spectrophotometer to get the absorbance measurement.

Partition Coefficient: For a given compound, its solubility between two solvents is given by the quantitative measure called the partition coefficient, which can be calculated given by the equation (1.5).

$$k = \frac{\text{Concentration of dye in ionic liquid}}{\text{Concentration of dye in aqueous phase}} \quad (1.5)$$

The partition coefficient values of the green and the yellow dye were calculated from the off-chip experiment for the given two-phase system. The k for green dye was found to be 34.3, whereas for the yellow dye was found to be 0.22. Thus, the green dye has much higher k value compared to the yellow dye, which indicates that the green dye molecules can be selectively extracted from a mixture of green and yellow dyes. This selective extraction of one analyte may lead to the separation of the compounds in the mixture.

The partition coefficient values of the green and the yellow dye were calculated from the off-chip experiment for the given two-phase system. The K for green dye was found to be 34.3, whereas for the yellow dye was found to be 0.22. Thus, the green dye has much high K value compared to the yellow dye, which indicates that the green dye molecules can be selectively extracted from a mixture of green and yellow dyes. This selective extraction of one analyte may lead to the separation of the compounds in the mixture.

Mixing Optimization for Higher LLE Yield

Different mixing schemes were studied, i.e., different ways of moving the two phases while they are merged to have the maximum extraction from the EWOD LLE process. The goal is to achieve a high extraction in a short amount of time. The higher the rate of transfer of molecules across the interface, the higher the LLE yield that can be obtained in a short duration. In this study, the sample consisted of one analyte, and its transfer to the extractant phase was studied under different mixing schemes. It is known in the art to that stretching the interface of the two phases enhances the extraction. The present study was done as an extension to this known technique to optimize and fix the mixing protocol with the highest yield possible on EWOD for all the following experiments.

The droplets generation and splitting were done using the same procedure described above. While mixing, an interesting phase phenomenon was observed. The phase with comparatively lower resistance to actuate often surrounded the other phase while mixing. In this case, the sample droplet with lower resistance to actuate with the addition of a surfactant surrounded the extractant phase. The quantification of the extraction yield for this study was performed off-chip using a plate-based spectrophotometer. The sample droplet after LLE on EWOD was collected and transferred to the spectrophotometer for concentration measurement.

Figure 13:
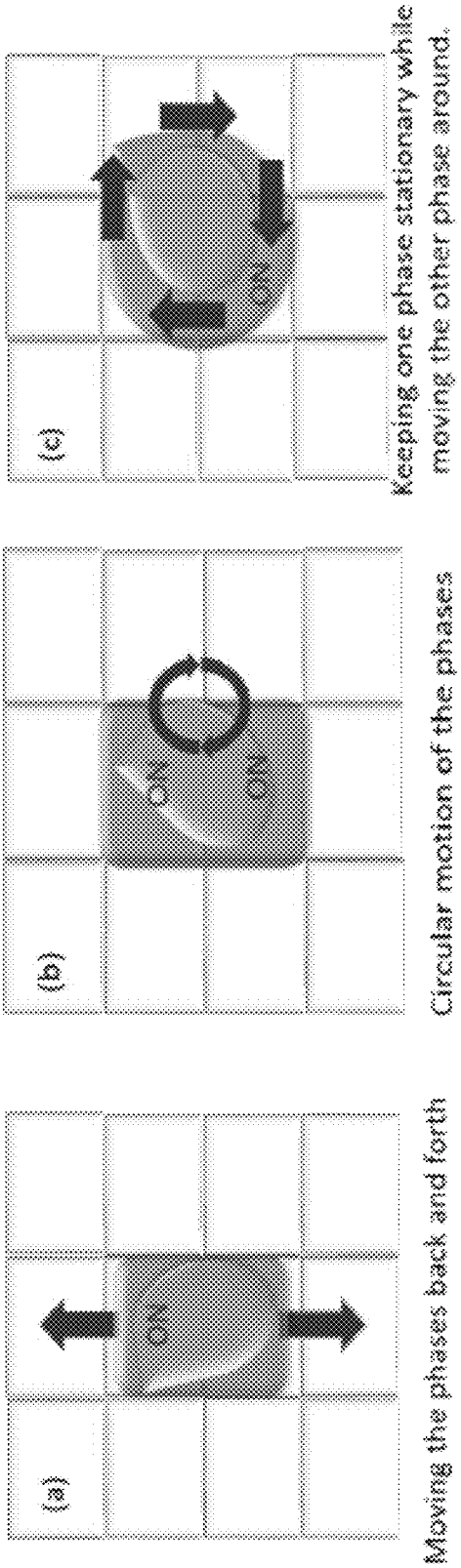
FIGS. 13A-13C show the three different mixing schemes for mixing dye molecules with the extractant when performing LLE.

FIGS. 13A-13C show the three different mixing schemes studied. The first scheme, shown in FIG. 13A, demonstrates the back and forth linear motion of the merged droplets. With this scheme of mixing, the dye molecules oscillated along with the droplets, and a very slow rate of diffusion into the extractant phase was observed. It was also observed that after some time, the interface between the phases would get concentrated, which further damped the transfer of molecules. The second scheme that was studied, shown in FIG. 13B, both of the phases were moved in a circular fashion, which enabled a higher rate of diffusion of the dye molecules into the extractant phase than the first scheme. The interface was observed to be less concentrated. The final scheme involved keeping the extractant droplet stationary and moving the sample droplet continuously around the sample phase, as shown in FIG. 13C. With this scheme of droplet motion, the relative velocity of the droplets was high, and the rate of the extraction was observed to be higher than the previous two schemes. However, the interface was observed to get concentrated after 1 minute of mixing. Based on all the visual observations of the rate of extraction during mixing and the final color of the sample after LLE, the most effective method was devised by combining schemes 2 and 3. In this method, the mixing was started by scheme 3, in which the sample phase was made to rotate around the extractant phase ten times, followed by mixing the droplets by scheme 2 for proper distribution of the extracted molecules in the IL phase. This method ensured the maximum extraction rate and also reduce the concentration of the interface during mixing.

Figure 14:
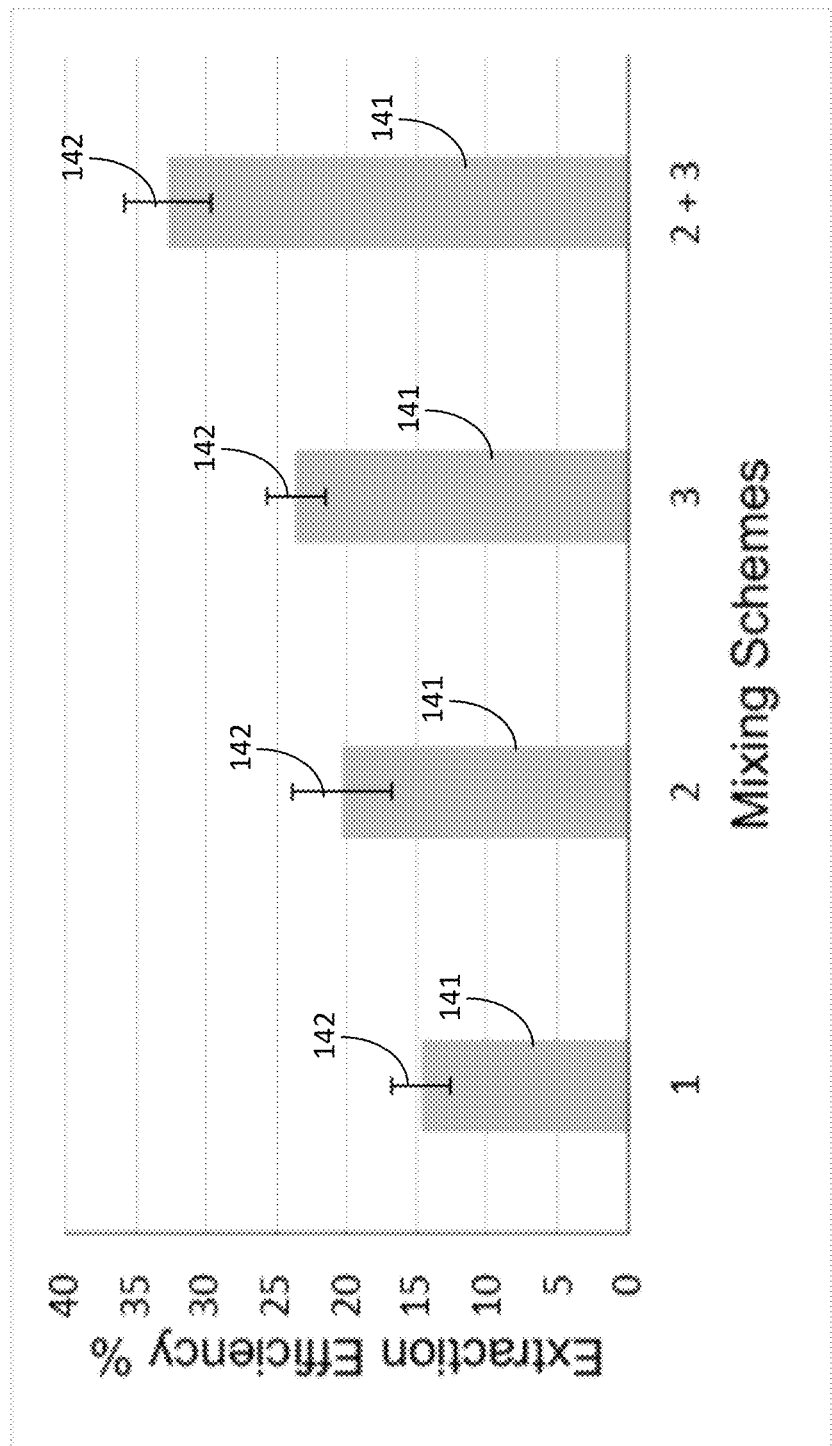
FIG. 14 is a bar graph of extraction efficiency plotted for each of the mixing schemes shown in FIGS. 13A-13C.

FIG. 14 is a bar graph of extraction efficiency percentage as a function of the mixing scheme used. The error bars 142 on each of the bars 140 in FIG. 14 indicate standard deviation using a total of three experimental repeats. Extraction efficiency was plotted for each of the mixing schemes by calculating the change in the sample concentration after LLE on EWOD. The extraction time for all the schemes was kept the same at 5 minutes to compare their yield. As was observed visually in real-time during the extraction process, the combination of the third and second scheme gave the highest extraction efficiency, the same was also obtained from spectrophotometer concentration measurement. On the other extreme, the extraction efficiency with the first scheme of mixing was found to be the lowest. Thus, it was concluded from the study of the effect of different mixing schemes on LLE that the combination of the third and second mixing schemes is the most efficient. This scheme of mixing was adopted for the other LLE studies on EWOD presented below in the present disclosure.

Separation of Binary Solution Mixture

Figure 15:
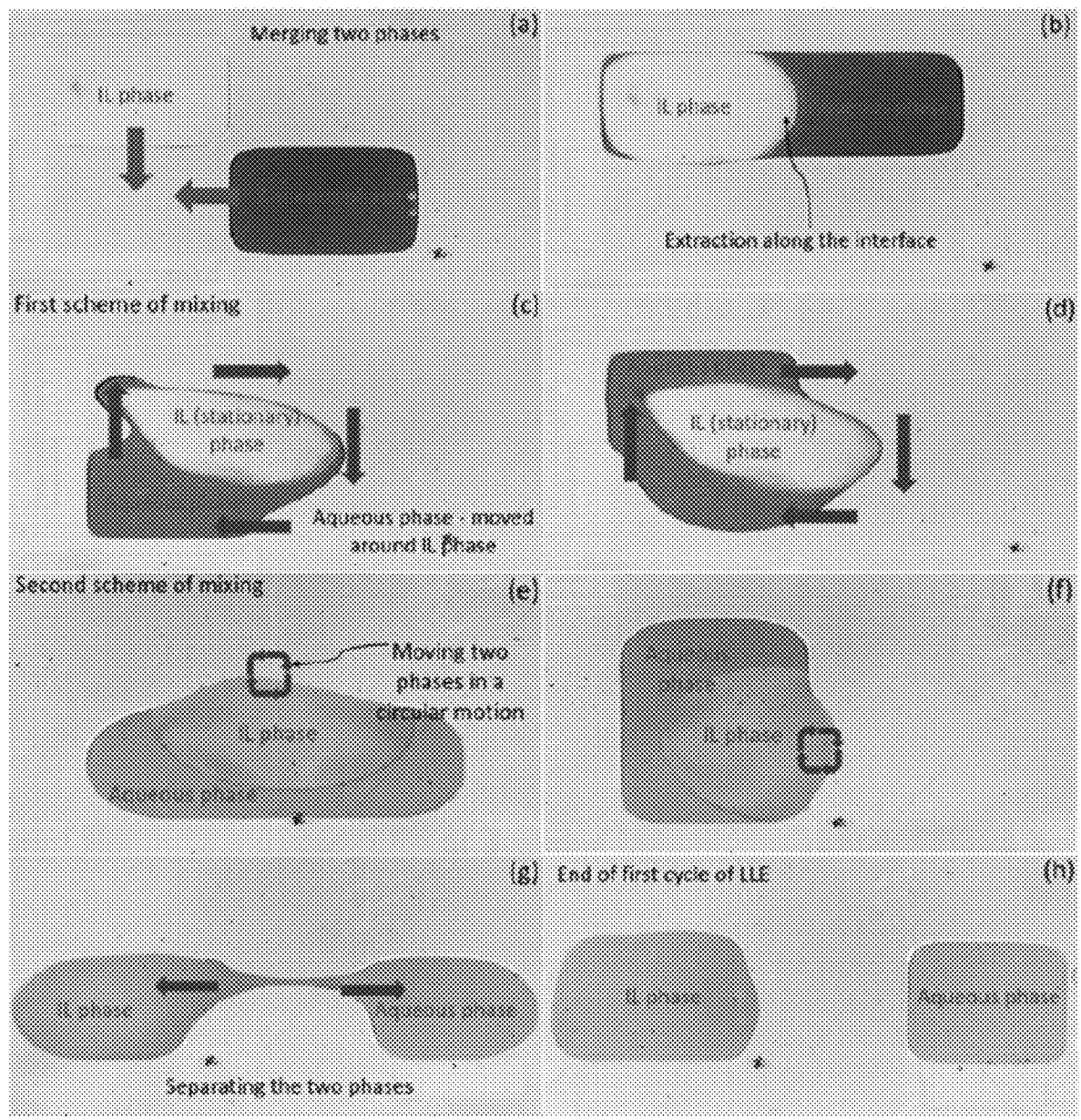
FIG. 15 contains snapshots (a)-(h) of various stages of LLE performed by the system shown in FIGS. 6 and 7 in accordance with a representative embodiment.

FIG. 15 contains snapshots (a)-(h) of various stages of LLE performed by the system 100 and described above for this study, including droplet generation, mixing and splitting. The sample and extractant droplets were originated from the reservoirs on the EWOD device 20. These droplets were approximately 200 nl in volume. The green dye molecules were selectively extracted from aqueous solution to IL, and finally, the droplets were split.

One of the observations made was that it was easier to drive the extractant phase compared to the sample phase. In other words, the higher the dye concentration, the more resistant was the sample towards the movement was observed. The difficulty of moving the sample droplet could be due to surface adsorption of solutes. This phenomenon has also been observed in the past for biofluids on EWOD devices. There are several proven solutions to the adsorption issue. One such known solution was tested by adding a 1% by volume of the surfactant Tween 20 to the sample. This modification significantly improved the movability of the sample phase so much that it responded even better to EWOD actuation than the extractant phase.

Once the formed droplets are driven along the electrode and merged, as shown in snapshot (a) of FIG. 15, the combined two phases can be mixed. The most efficient mixing scheme was adopted (FIG. 15, snapshots (c)-(f)). Almost all the green dye color was extracted to the IL drop within 5 minutes while mixing.

The next step is to split the two phases, as shown in snapshots (g) and (h), which is a critical part of this LLE device. There have been several studies reported on cutting a liquid drop into two droplets on EWOD devices. The general procedure to split a liquid drop using electrowetting forces is to elongate it over three electrodes by wetting at two ends and keeping the middle electrode nonactivated (0 V). The liquid flows to the wetted area, and a neck is formed in the middle. The present study attempted cutting a drop formed by two liquid phases instead of a single-phase droplet. As the two liquid phases have different interfacial properties, the surface tensions, the pressure differences at the interfaces, are usually different. Consequently, the two phases move at different velocities. Therefore, moving two phases onto two separate electrodes requires an intuitive way of activating the electrodes. In previous work, it was reported that the slower phase should be moved first and located on the desired electrode. Once the two phases are placed on two opposite electrodes, as shown in snapshot (g) of FIG. 15, applying a sudden impulsive potential by turning the electrodes on and off simultaneously causes phase splitting, as shown in snapshot (h).

The most important observation was that the merged body tends to break into two equal volumes rather than breaking at the interface of the two phases; hence, the successful splitting (without any residues from each other's liquid phase) of two phases depends on the relative volumes of the two phases. When either the extractant or the sample droplet is slightly larger in volume than the other, splitting creates some residue in the droplet of smaller volume. According to these observations, splitting of these two particular liquid phases seems to be similar to dividing a single-phase parent droplet into two daughter droplets. Thus, it has been shown that two merged immiscible liquid drops, after a liquid-liquid extraction with a 1:1 sample-to-extractant volume ratio, could be successfully separated on the EWOD device 20. Some reports have indicated that the droplet movement is biased toward an electrode activated with a higher voltage compared to the voltages applied on surrounding electrodes. Snapshot (h) shows the two split phases with the components of the solution mixture separated.

On-Chip Concentration Measurement

Figure 16:
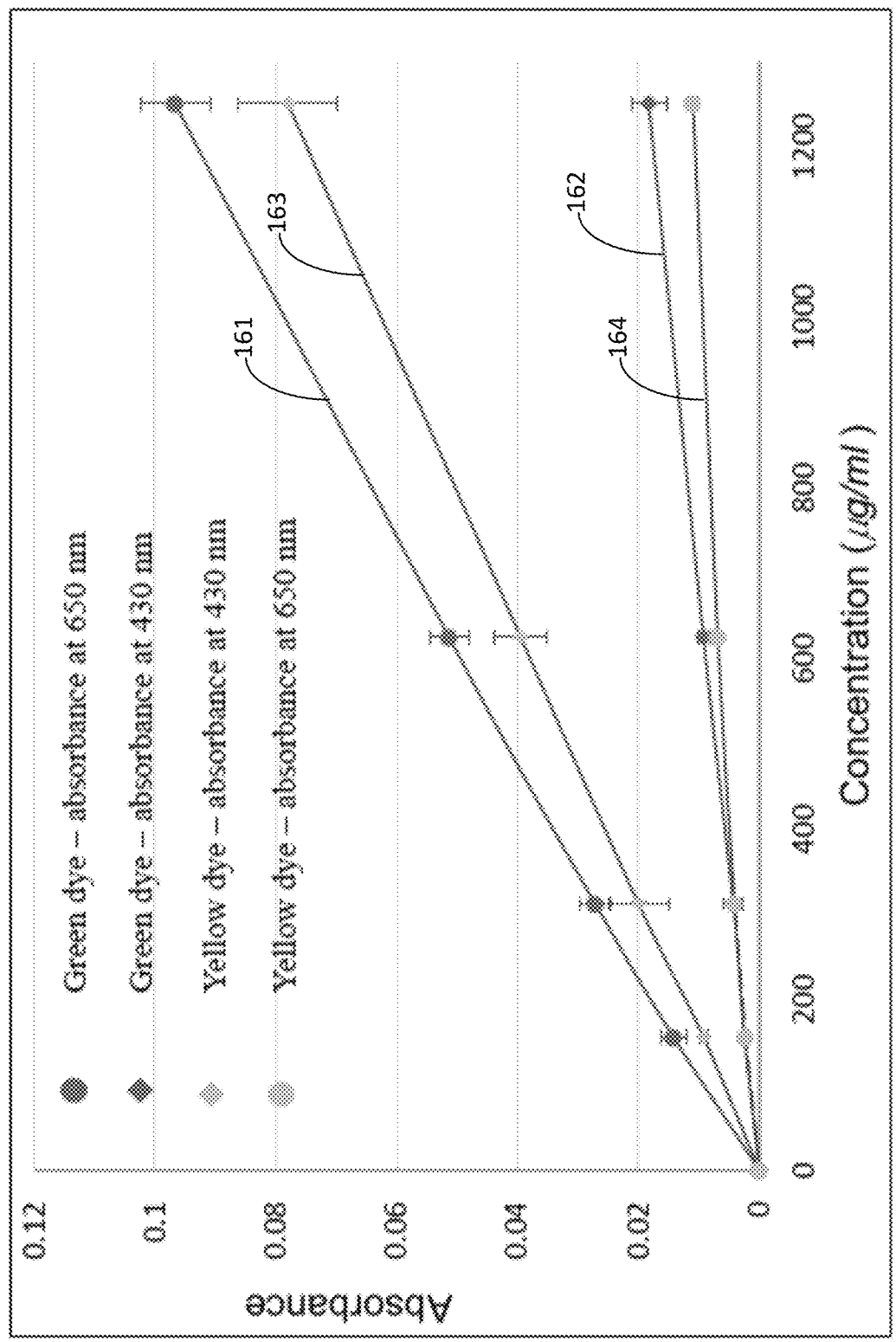
FIG. 16 is a graph change in the absorbance values of green and yellow dye solutions with concentration when exposed with the different wavelengths of light.

FIG. 16 is a graph of concentration vs. change in absorption for the data obtained for calibration using the steps outlined above was plotted. It shows the calibration curves for the green and yellow dye solution on the EWOD chip.

The plot 161 shows the change in the absorbance values of green dye solution with concentration when exposed with the 650 nm light source and the plot 162 shows the absorbance values of green dye solution with concentration when exposed with the 430 nm light source. Similarly, the plot 163 shows the change in the absorbance values of the yellow dye solution with the concentration when exposed with the 430 nm light and plot 164 shows the absorbance values of yellow dye solution with concentration when exposed with the 650 nm light source.

As is seen from the calibration curves 161-164, the green dye has more absorbance for 650 nm light, and the yellow dye for 430 nm light, as was also found in the plate-based spectrophotometer with the off-chip measurements. Though the green dye has less absorbance for the 430 nm light and the yellow dye has less absorbance for the 650 nm light, their respective calibration curves are a requirement when working with a binary mixture solution, as discussed above.

Multistage LLE on EWOD

Multi-stage LLE (MLLE) is a process where the same extraction steps are repeated to increase the recovery of the target analytes. One of the primary advantages of EWOD devices are their ability to run continuous, multistep processes. When there is a limited transfer of solute in a single step or cycle of LLE, MLLE can be performed on EWOD microfluidics. In the present study, since there is a vast difference between the partition coefficient of each of the analytes, the MLLE process on EWOD could lead to better separation results for analytes in the binary mixture.

In order to explore this characteristic of EWOD, MLLE was performed in this study with two cycles of LLE. The protocol for the first cycle of LLE was the same as described above with reference to FIG. 15. In the second cycle of LLE, a fresh extractant (IL) droplet was generated from the reservoir, and the LLE steps were repeated. After each cycle of the process, the sample droplet was transported to the concentration measurement electrode, and the voltage measurement was done for absorbance.

Figure 17:
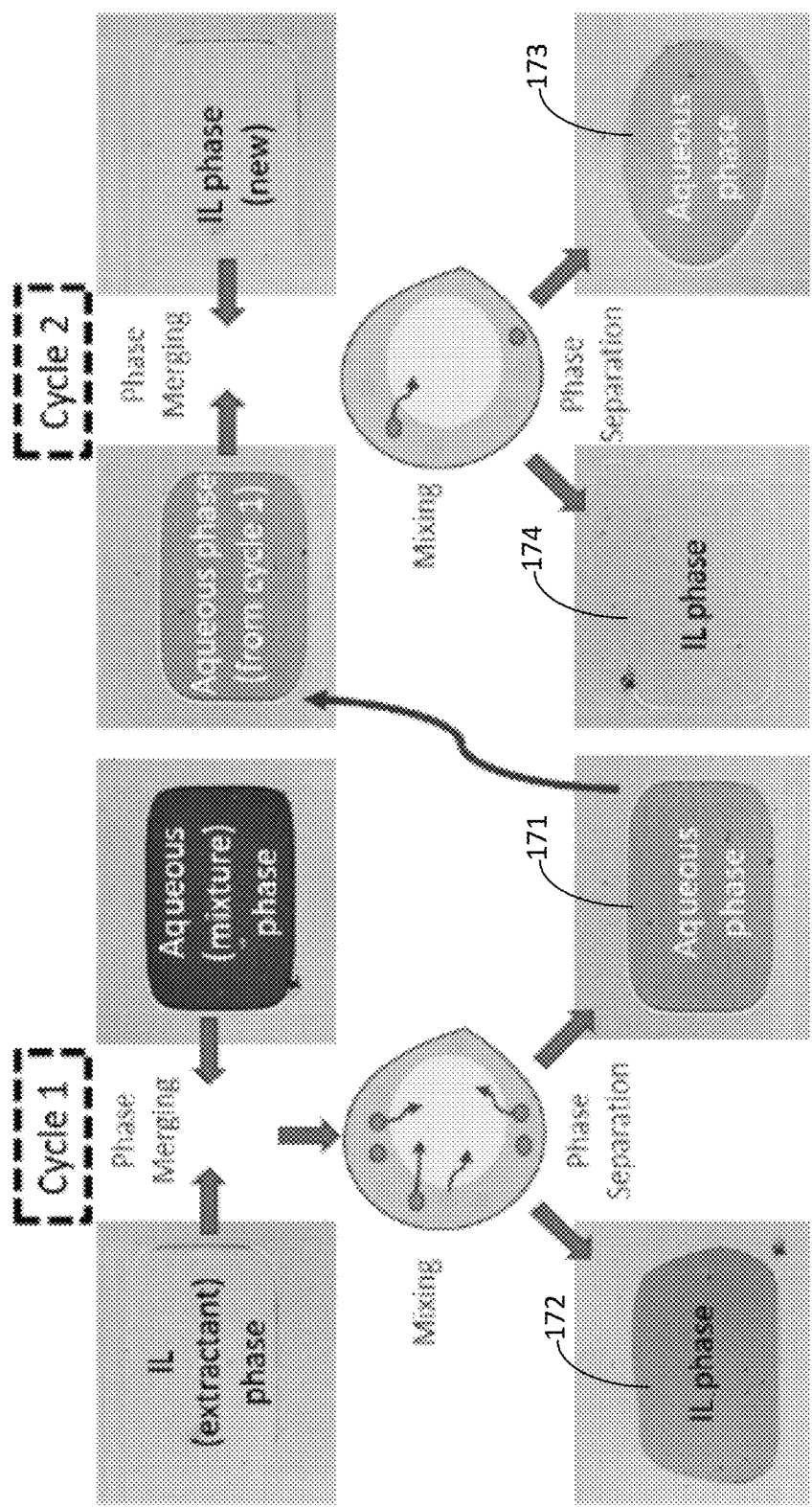
FIG. 17 is a diagram depicting the process flow for two LLE cycles that shows changes in the color of the sample and extractant droplets before and after each LLE cycle.

FIG. 17 is a diagram depicting the process flow for two MLLE cycles that shows changes in the color of the sample and extractant droplets before and after each cycle of MLLE. As is seen in FIG. 17, the sample droplet 171 becomes much less concentrated with green dye molecules and appears somewhat yellowish, whereas the extractant droplet 172 appears lighter green with most of the green dye extracted. The extraction rate was observed to be very high, given the high concentration gradient between the two phases. It was observed in some experiments there was a decrease in the sample volume phase after the first cycle of MLLE, resulting from evaporation during the experiment. Thus, the processing time for each cycle was optimized to minimize the loss of sample volume.

In FIG. 17, the image results from the second cycle of the MLLE process show that the final sample drop 173 has very few green dye molecules and is mainly concentrated with the yellow dye, whereas the extractant droplet 174 again turns a little green extracting the rest of the green molecules left after the first cycle of LLE. Further decrease in the volume of the sample was observed at the end of the MLLE process resulting from evaporation, as can be seen in FIG. 17. The evaporation can be damped by controlling the vapor pressure of the surrounding environment of the droplet. With the decrease in the concentration gradient, during the second cycle, the extraction rate was observed to be quite low compared to the first cycle, with also very few molecules being extracted.

Figure 18:
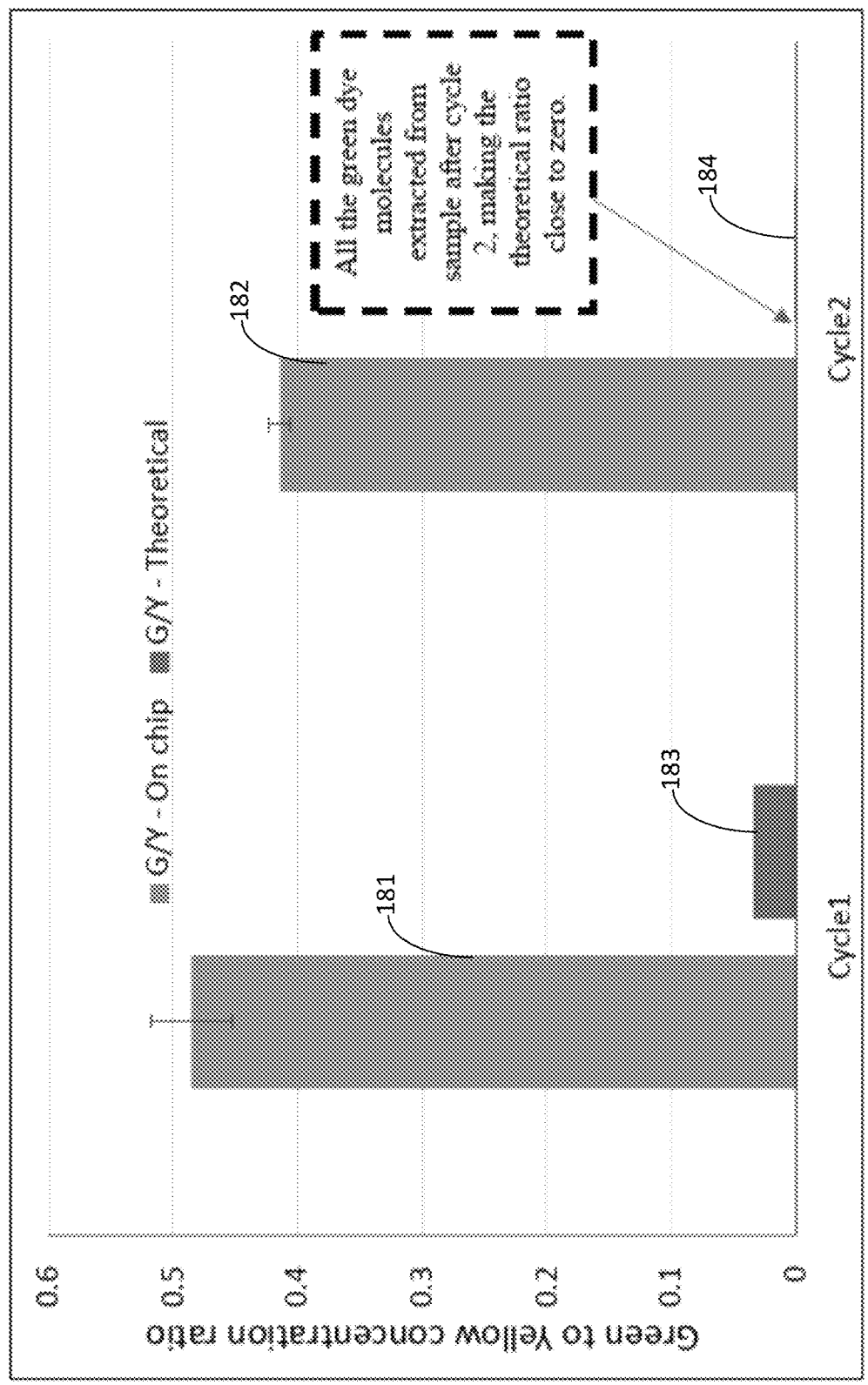
FIG. 18 illustrates a bar graph of the cycle number vs. the green-to-yellow concentration ratio for the multi-LLE (MLLE) process depicted in FIG. 17.

Next, the results of binary separation by MLLE performed on the EWOD device 20 was compared with theoretical values. The theoretical values were calculated from the partition coefficient values of each solute obtained in the manner described above. FIG. 18 illustrates a bar graph of the cycle number vs. the green-to-yellow concentration ratio for the MLLE process depicted in FIG. 17. The drop in the sample concentration ratio of green to yellow dye after each cycle of on-chip LLE and the theoretical values. The bars 181 and 182 represent the change in the concentration obtained from the on-chip experiments for the first and second cycles, respectively, whereas the bars 183 and 184 represent the theoretical concentration ratios for the first and second cycles of MLLE, respectively.

The sample phase was prepared with concentration ratio 1:1 at the beginning of the process, and with each cycle of MLLE, the ratio decreases, as indicated by the bar 182 being shorter than the bar 181. A sharp decrease in the concentration ratio is observed after the first cycle of LLE on EWOD. Almost 50% of the green dye was extracted during this step in an extraction time of 5 minutes. The extraction rate was observed to be very high during the first cycle. The drop in the concentration ratio after the second cycle is not as significant as the first cycle. At the end of the second cycle, almost 60% of the initial green dye was extracted, and the concentration ratio drops to 0.4 by the completion of the MLLE process. The extraction rate in the second cycle was much less compared to the previous cycle. The error bars in FIG. 18 indicate standard deviation using a total of two experimental repeats.

The difference in the LLE performance in the EWOD and tube-scale experiments, as illustrated in FIG. 18, can be attributed to the fact that the mixing of the two phases is limited in the micro-scale system given by the low Reynolds number. On the macro scale, the phases undergo a turbulent mixing performed by vortexing to achieve the maximum extraction. Similar problems associated with mixing at the microscale have also been reported elsewhere. Also, because of the evaporation problem, the extraction time was not very long, as with longer extraction time, the sample tends to lose its volume.

The results point out that one type of molecule can be separated from the other in a binary solution with LLE on a DMF device. As shown, acid green undergoes more extraction through LLE cycles than yellow dye, proving that this method leads to complete separation of binary mixture solution. Thus, using LLE on EWOD, such a binary mixture of different solutes was successfully separated in this study owing to the different affinity of the solutes for the extracting phase.

Conclusions of the First Study

A microfluidic LLE method of separation of compounds in a binary solution is demonstrated in this study. The solutes separate according to their affinity towards respective fluids. For instance, the affinity of the acid green dye is higher towards ionic liquid. This property causes separation of the acid green dye rapidly from the reactive yellow in the aqueous phase. The mixing of two phases, which is critical for a successful LLE process, was studied. The splitting of the merged liquid phases at the end of the process occurred in a similar way as breaking a single-phase mother drop into two daughter droplets.

The conventional spectrophotometry method to measure absorbance was used for the concentration measurement of each solute. In order to perform the concentration measurement on a chip, the EWOD device was integrated with LED light sources and a photodiode. MLLE was successfully demonstrated on this device for higher recovery of the green dye from the sample. This platform can be used to optimize the number of cycles required for higher separation of different analytes in the MLLE process, instead of performing standard laborious lab-scale experiments.

When the on-chip protocol is fully utilized with its downstream assay capability, it will provide a versatile sample preparation platform. This method can be also be applied towards separation and purification of compounds of interests (e.g., target proteins, DNA) from a complex solution such as raw blood samples for applications in chemical and biochemical analyses. In the subsequent studies disclosed herein, this platform is examined for the separation of DNA molecules from its other cellular components.

Second Study

Magnetic-Bead-Free DNA Extraction Enabled by EWOD Digital Microfluidics

DNA extraction represents a significant bottleneck in the nucleic acid analysis workflow. With many of the nucleic acid assays being automated thanks to the advancements in fluidics and miniaturization, the DNA extraction protocol is much needed to be integrated into these systems as a sample preparation step for a quick sample-to-result solution. This study is the first study of on-chip DNA isolation without the use of magnetic beads in EWOD DMF. Instead of using magnetic beads, LLE was employed. In a first part of this study, an aqueous sample droplet of pure plasmid DNA (pDNA) was introduced on the EWOD platform, and an IL was used as the other extractant phase. All of the steps—dispensing, merging, mixing, and splitting of the phases were performed on the EWOD platform described above with reference to FIGS. 5-7. The ease of handling of the two-phase liquid system on this platform makes this integration possible. The selective DNA extraction was also achieved from a DNA-protein mixture solution. The quantification of the on-chip LLE process was done by measuring the sample concentration before and after LLE by using an off-chip instrument.

The second part of this study is the first attempt for performing DNA LLE from other impurities, such as protein molecules performed on the EWOD platform in a DTD format. It is known to use EWOD platforms for the DNA extraction process, but such platforms make use of the magnetic bead-based extraction technique and complex protocols on-chip. By using the LLE method of DNA extraction in accordance with the inventive principles and concepts, the need to use magnetic beads and external magnets is obviated, and the DNA isolation process is performed in fewer, simpler steps.

The use of the EWOD platform disclosed herein has an advantage over traditional continuous microfluidics in moving droplets individually, and thus a liquid handling platform is achieved where each liquid droplet phase can be accessed and manipulated. This functionality of EWOD enables the merging of the two phases (sample and extractant), the user-defined mixing time, and ease of splitting of the phases after the LLE process, as discussed above. In addition, the ease of integration of other downstream nucleic acid assays on this platform makes it an excellent choice for a sample-to-result platform for various applications. The first part of this study includes the LLE of DNA molecules from a control sample containing only pDNA molecules to show the working of the LLE process on EWOD. The second part of this study involves the selective extraction of pDNA from a binary mixture of pDNA and BSA protein molecules in the sample. IL was used as an extractant in the second and third studies.

Experimental
Reagents

For this study, pDNA pVAX1-hVEGF165 transformed in growth strain DH5-Alpha, obtained from Addgene, was used as the model DNA. Details of the pDNA are provided below. The bacterial strain was cultured to increase the colony, and from the expanded colony, pure pDNA was extracted using the Qiagen Hispeed kit for all the control LLE experiments. BSA protein was used as the impurity molecules to show the selective extraction of pDNA from a binary mixture of pDNA and protein. Commercially available IL BMIM-PF6 (same as used in the first study) was chosen as the extractant phase. Ethidium bromide (EtBr; Life Technologies, Gaithersburg, Md.) was used as received for intercalation with DNA for qualitative analysis of on-chip LLE.

Device Design, Fabrication and Control

Detailed fabrication steps with the layout of the platform and all the different layers of the chip were described above, as was the experimental setup and the control parameters.

Plasmid DNA Introduction pDNA are small, circular, double-stranded DNA molecules that are different from cells genomic DNA (gDNA) and are present in bacterial cells, and some eukaryotes. Usually, they exist as a supercoiled structure. The pDNA used in this study has a vector backbone pVAX1 with a size of 3000 bp, and the inserted gene is hVEGF165 with a size of 578 bp. pDNA was used as the model DNA molecule for this study, and the same approach can be extended for the extraction of other targets nucleic acid such as genomic DNA from sample lysate.

Besides, using pDNA as a model DNA for a proof of concept LLE study, pDNA extraction on EWOD finds application when the downstream process is a gene-editing system (transformation or transfection) on-chip. pDNA has been the point of interest in many gene delivery studies where target genes are transferred with pDNA to the targeted tissue. The success of this protocol is measured by achieving a stable transfection, i.e., more pDNA containing the inserted gene should reach the nucleus of the target cells surviving enzymatic degradation for efficient transfection and protein expression studies are done subsequently. The reported studies so far have integrated the downstream protocols such as pDNA transformation in bacterial cells on EWOD with the pDNA extraction done off-chip. The sample preparation step (pDNA extraction) presented in this work can be integrated with the downstream protocols (i.e., the transformation of bacteria) to have the complete workflow in one platform.

Plasmid DNA Production

For all of the control experiments, pure pDNA was obtained using a Qiagen Hispeed kit from the bacteria pellet. Plasmid DNA transformed in *E. coli* strain was expanded to increase the bacterial colony using standard techniques, as described below.

A bacterial stab of *E. coli* containing the plasmid pVAX1-hVEGF165 obtained from Addgene was streaked on a Kanamycin-agar plate. After overnight incubation at 37° C., individual colonies were picked from the plate into starter cultures. One of the starter cultures were expanded into a 250 ml LB Broth supplemented with Kanamycin and incubated overnight in 37° C. shaker. After overnight culture, the bacterial pellet was collected by centrifugation of the 250 ml culture. This pellet was then used to extract the plasmid using Qiagen Hispeed midi prep kit. There are many lysis processes that can be done. In this study, chemical lysis, as directed in the Qiagen kit protocol, was adopted. The lysis process ends with the precipitation of the denatured proteins, cell debris, and other nucleic acids. Then a filtration step was adopted to filter out the lysate or supernatant from the impurities. In the second filtration step, the pDNA is eluted along with some other impurities. The third filtration step involved washing the pDNA with ethanol to eliminate the impurities and finally eluting the pure pDNA from the filter with the help of ultrapure water. The DNA sample was then checked by measuring the concentration and purity of the pDNA. Pure pDNA obtained from this workflow was used for all the control experiments.

DNA Quantification Instrument

The DNA quantification was done by using the NanoDrop™ instrument both for the on-chip and tube-based off-chip experiments. The concentration of the DNA sample obtained from the Qiagen kit was measured. Based on the readings of the NanoDrop™, the sample was found to be of pure pDNA with no impurities (RNA, proteins, etc.). For the LLE experiments, the DNA left in the aqueous phase was measured to quantify the yield of the process.

It was observed from the off-chip experiments, that after the LLE process, the sample showed a sharp peak at 230 nm wavelength higher than the peak at 260 nm (wavelength of highest absorptivity of DNA molecules). This peak comes from the ions absorbed by the sample phase from the IL during the LLE process. The following procedure was adopted to decrease the peak at 230 nm and increase the resolution of the measurement at 260 nm wavelength. Instead of using ultra-pure water as the blank for all the DNA concentration measurements, the ultra-pure water was first mixed with the IL and then split as done in the LLE process and used as the blank. In this process of mixing the water with the IL, some of the ions diffuse into the water phase. The water phase after splitting from the IL phase used as the blank has ions from the IL and was used in all the concentration measurements. This method helped to suppress the peak at 230 nm and increased the resolution of the peak at the desired 260 nm for the sample DNA concentration measurements.

For the EWOD LLE experiments, the sample after the extraction was collected and transferred to the NanoDrop™ for concentration measurement. However, the volume of the sample droplet was too small (~400-500 nl) from a single LLE test for the NanoDrop™ measurement. Three tests were conducted under the same experimental conditions, and the sample droplets were merged to increase the volume. The increased sample volume was used for the concentration measurement, which is an average of three on-chip LLE experiments, and thus, one data set was obtained. The final concentrations of the sample after LLE were compared with the initial concentration to find the amount of pDNA transferred to the IL phase.

Off-Chip LLE Experiments

DNA LLE tests were conducted off-chip (in tubes) to find the extraction efficacy of the IL used in this study. A control sample of 100 ng/µl of pDNA was prepared and mixed with an equal volume of IL in a 1 ml tube. The mixture was mixed vigorously with constant shaking. After mixing, the phases were allowed to settle back, and the top sample phase was pipetted out and transferred to NanoDrop™ for concentration measurement.

In the past, the use of BMIM-PF6 was demonstrated to be an excellent candidate for the extraction of DNA from both pure DNA samples and a sample containing other impurities. Almost 100% extraction of DNA from the aqueous phase was observed, and from that, 30% of DNA obtained after back extraction from IL to an aqueous phase. The mechanism of extraction involved electrostatic interactions between the negatively charged phosphate group of DNA and the cation of the IL. However, it has been reported that this IL is more suitable for DNA staining dye extraction and the successful extraction of dye molecules from a DNA-dye mixture sample. Similar to those studies, tube-based DNA LLE experiments were conducted, and the residual DNA concentration in the aqueous phase was measured.

It was reported previously that the co-extraction of protein was not observed using this IL. In the current study, experiments were performed to study the extraction of BSA protein with BMIM-PF6 separately in the off-chip LLE experiment. In this experiment, pure BSA protein was mixed in ultra-pure water as a control sample, and the concentration was adjusted to 100 mg/µ. The solution (sample phase) was then mixed with an equal volume of the IL in a 1 ml tube. The sample was mixed vigorously for 5 minutes and then left to settle for the phases to separate. The top sample phase was carefully separated and was transferred for quantification by NanoDrop™ using 280 nm wavelength. The LLE experiments confirmed that no protein was extracted, more detailed results below. It was concluded from this experiment that when pDNA and BSA molecules are mixed in a sample, the IL can selectively extract pDNA molecules from the mixture, and for all the on-chip LLE experiments, only DNA concentration in the sample was quantified.

On-Chip LLE Experiments

The protocol for on-chip DNA LLE was the same as described above with reference to FIGS. 5-8. Briefly, the sample droplet and an IL droplet were generated from two different reservoirs and were merged to initiate the mixing process. In this study, the optimized mixing scheme described above with reference to FIGS. 13A-15 was adopted. The end step of LLE is to split the two phases, and they can now go for their respective downstream analysis. After the LLE process was performed on the EWOD device 20, the sample was transferred to Nanodrop™ for DNA concentration measurement.

Before moving to the LLE experiments on-chip, it was confirmed that the pDNA lost in the sample was a result of on-chip extraction and not due to device surface adsorption. A study was conducted to quantify the DNA lost to the device surface due to EWOD motion. Different sample concentration droplets were moved on the chip using EWOD operations without LLE. The droplets were moved on four electrodes in a back and forth motion for 15 minutes, which was the maximum time duration of the LLE process that was studied on EWOD. After moving the droplets on the EWOD device, they were transferred to NanoDrop™ to measure the concentration lost to the surface of the device. From this study, it was found when a sample concentration of around 100 µl was used, there was no adsorption by the surface due to EWOD motion. Sample concentration higher than 100 µl in the range of 200 µl or higher was found to lose some of the DNA molecules to the surface. The detailed results are shown and discussed below.

The first DNA LLE study was conducted to show the on-chip LLE of pDNA from a sample containing pure pDNA. The motivation for this study was to show the concept of transfer of DNA molecules in a DTD format using the EWOD platform. A sample concentration of 100 µl was used for this study.

The second on-chip LLE study was conducted to show the capability of the platform to extract DNA selectively from its other impurities. The sample was prepared by spiking BSA protein in the pDNA sample and hence, creating a mixture of pDNA and protein. The sample concentration was adjusted such that each analyte had a final concentration of 100 μl in the mixture.

Results and Discussion

Off-Chip LLE Experiments

The concentration of the residual DNA left in the sample undergoing off-chip LLE was measured. The off-chip LLE experiment from pure pDNA samples showed an extraction efficiency of 30%. The percentage yield was sufficient to demonstrate the capability of EWOD DMF for LLE of DNA using this IL.

The second off-chip study was done to check the extraction of protein molecules by the IL phase. The protein quantification mode (expose the sample to a wavelength of 260 nm) was chosen in the NanoDrop™, and the sample phase was tested. There was no change in the concentration of the protein in the sample before and after the LLE process. Hence, no protein extraction was observed using the IL as the extractant. A pH of 6.9 for the sample (BSA protein mixed in ultra-pure water) was maintained for this experiment. The isoelectric point of BSA molecules was found to be 4.8 from the literature, and given the pH of the environment, the protein molecules should have a small negative charge on them. However, the electrostatic interaction between the charged BSA molecules and the ions of the IL was not strong enough to extract the protein molecules to the IL (extractant) phase. From this experiment, it was concluded that for all the on-chip experiments, if the same conditions are maintained, there will not be any protein co-extraction.

Absorption on Chip Surface Due to Droplet Motion

Figure 19:
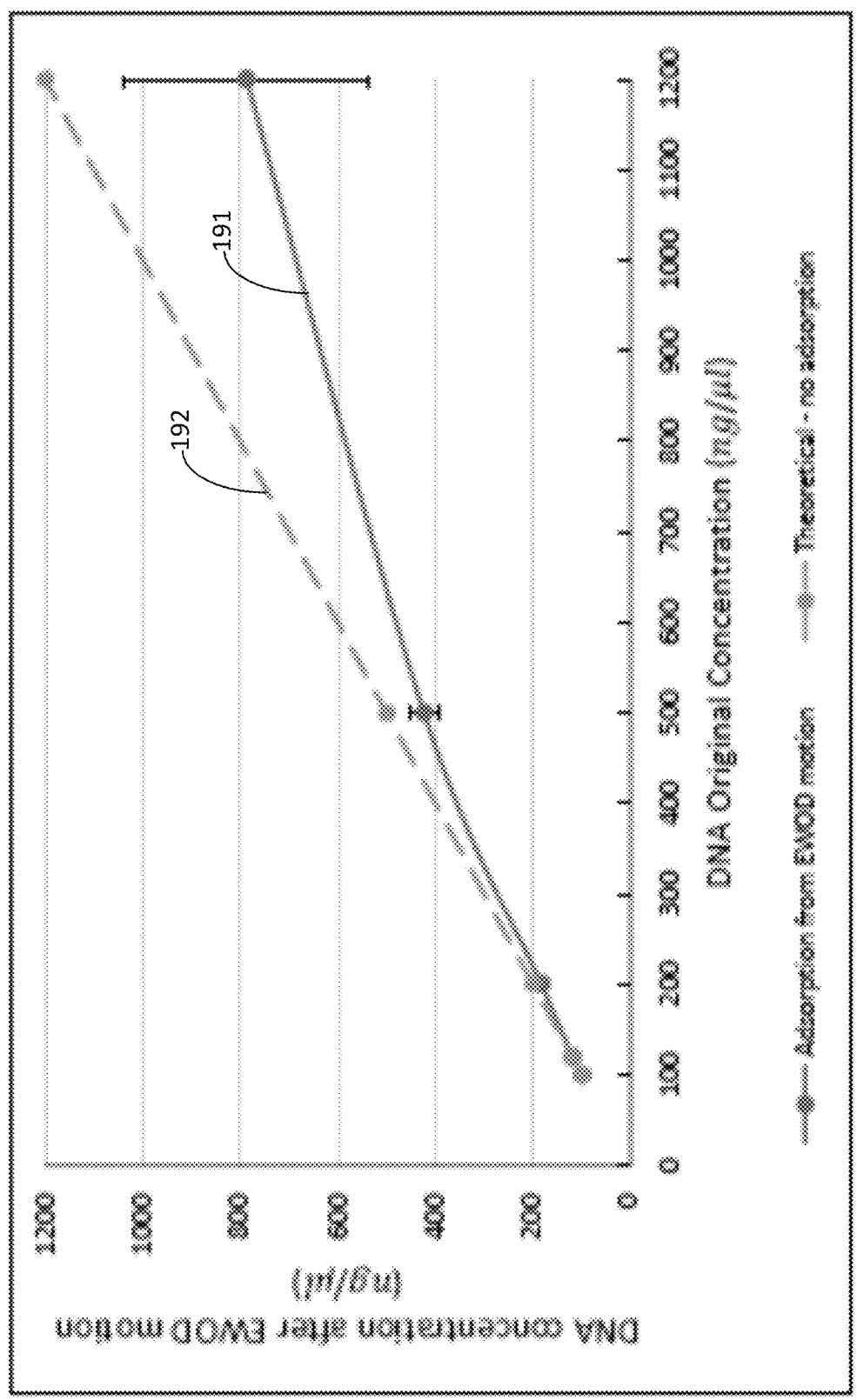
FIG. 19 shows the comparison of DNA concentration before and after EWOD motion using the system shown in FIGS. 6 and 7.

To find a concentration of DNA that would not be adsorbed by the EWOD surface, and to confirm that the change in the sample concentration is coming from on-chip LLE, motion tests were conducted with different concentrations of DNA sample. The results of this study are plotted in FIG. 19. FIG. 19 shows the comparison of DNA concentration before and after the EWOD motion. The vertical axis represents the DNA sample concentration tested, and the vertical axis represents the concentration after EWOD motion. The curve 191 represents the sample concentration tested on EWOD. In the ideal situation, DNA should not be adsorbed on the surface, which is represented by the reference line 192 in FIG. 19. Any experimental data point which does not fit the reference line 192 is discarded to be used in further LLE experiments. It was found that with concentration close to 100 there was no loss of DNA due to EWOD motion. As can be seen from the results, the samples of concentration 500*D+)(and 1200*D+)(there was a significant change in the concentration with a higher standard deviation due to surface adsorption. A loss in the sample volume was also observed while retrieving samples from the chip with higher concentration. Hence, it was concluded that a sample concentration of 100 ng/μl or less was suitable for the LLE experiments. All of the on-chip LLE experiments were done at an initial sample concentration of 100 ng/μl.

The system 100 comprising the EWOD device 20 was successful in generating the sample and IL phase droplets of equal volume, transporting the droplets to the mixing and extraction zone, and finally split the two phases to complete the LLE process. The optimized mixing, as described above, was adopted for all the experiments. Similar to the first study, it was observed that the droplet, which was easy to actuate with EWOD forces, would engulf the other phase. In this study, the IL phase was more mobile than the sample phase under the voltage application and hence, completely engulfing the later phase. During mixing, in this study, the sample phase was kept stationary, and the IL phase was made to rotate around the sample phase. The snapshots from the experiment of the entire protocol are shown in FIGS. 20A-20E.

Figure 20A:
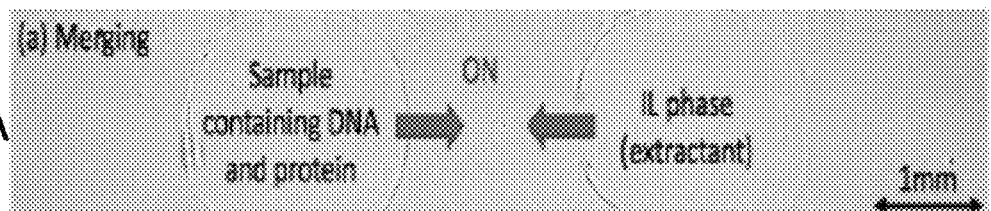
FIGS. 20A-20E illustrate snapshots of LLE on the EWOD device shown in FIG. 5 at various stages of the process in accordance with a representative embodiment for selective extraction of pDNA from a binary mixture of pDNA and BSA protein molecules in the sample.
Figure 20B:
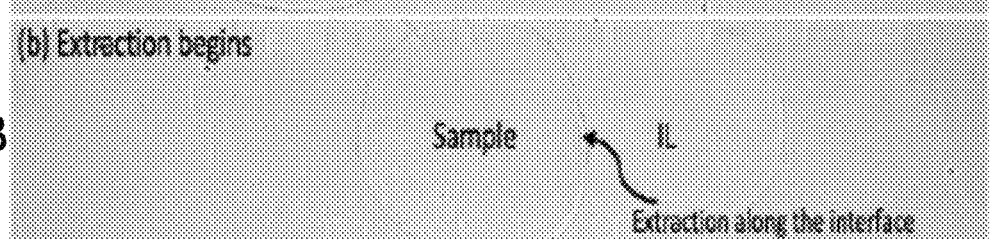
Figure 20C:
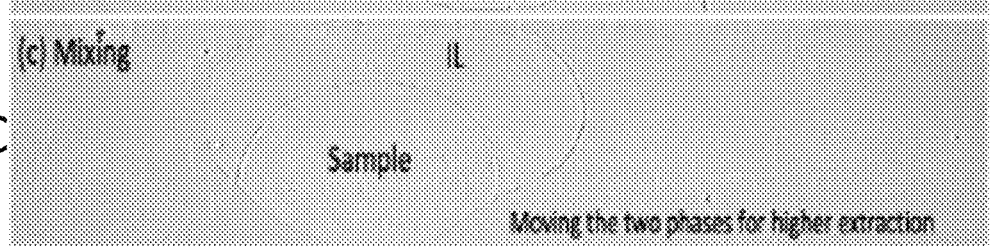
Figure 20D:
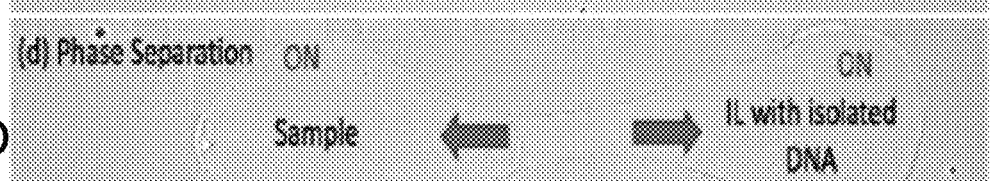
Figure 20E:
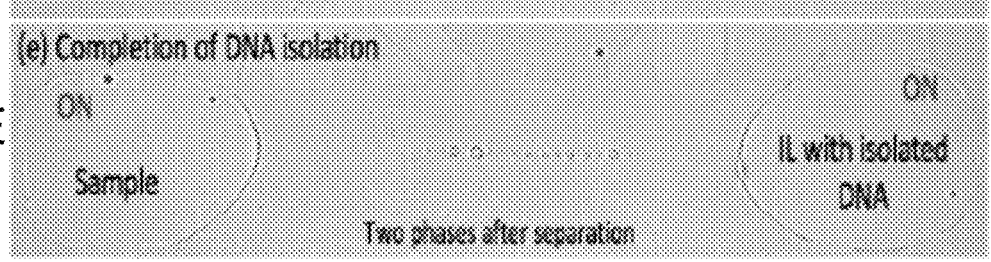

FIGS. 20A-20E illustrate snapshots of LLE on the EWOD device at various stages of the process in accordance with a representative embodiment for selective extraction of pDNA from a binary mixture of pDNA and BSA protein molecules in the sample. FIG. 20A shows a snapshot of the sample phase and the IL phase during merger of the phases; FIG. 20B shows a snapshot of DNA extraction taking place along the interface of the phases; FIG. 20C shows a snapshot of the phases as they are moved around to increase mixing and extraction; FIG. 20D shows a snapshot of the phases as they are being separated to conclude LLE; FIG. 20E shows a snapshot of the separated phases, allowing the sample to be collected for concentration measurement using Nanodrop technology.

The EWOD device 20 was used to manipulate the sample droplet containing the DNA and the IL droplet. All the steps of LLE were performed—the droplets were merged (FIGS. 20A and 20B) and mixed (FIG. 20C) for the DNA to move from the sample phase to the IL phase. This was followed by the splitting of the two phases (FIG. 20D) to conclude the LLE process (FIG. 20E). The quantification was done off of the EWOD device 20 using a Nanodrop™ instrument and on-chip (on the EWOD device 20) fluorescent images were also taken to demonstrate the DNA extraction. The Nanodrop™ instrument that was used for this purpose is a Nanodrop 1000 manufactured by Thermo Scientific.

On-Chip DNA LLE— Fluorescent Image

Figure 21:
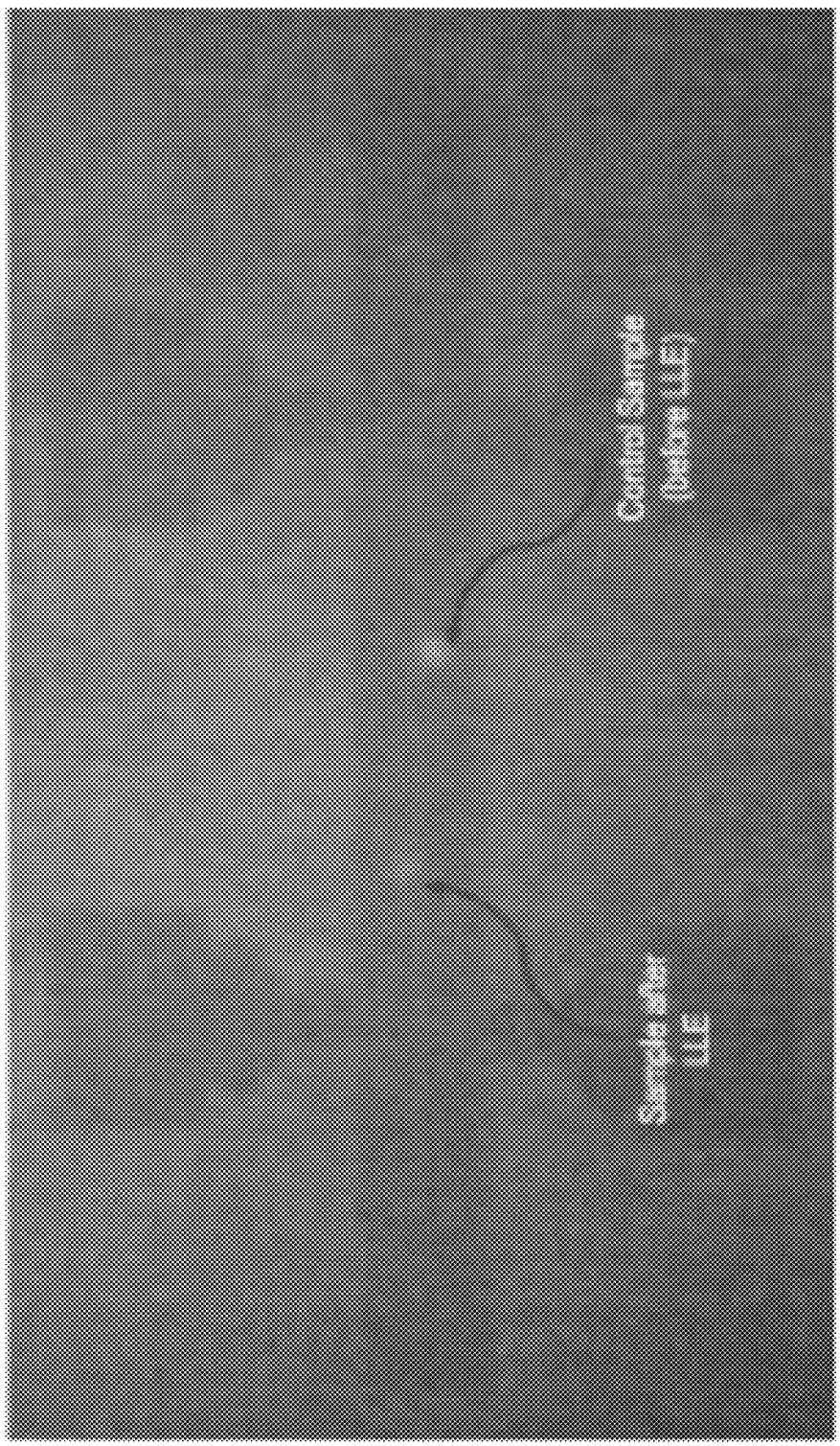
FIG. 21 shows a change in fluorescent intensity of a sample after the pDNA extraction has been performed using the EWOD device shown in FIG. 5.

The fluorescent images that were captured on-chip were compared with a control sample to obtain a qualitative result showing the extraction happening from the pDNA sample by the LLE process on-chip. After the LLE process, an EtBr dye droplet was mixed with the sample on-chip. The intercalation of DNA-EtBr increases the fluorescent intensity when exposed to a wavelength of 285 nm ultraviolet light. The same concentration of EtBr was added to a sample droplet that did not undergo LLE. The device was then taken to a gel doc instrument, and a fluorescent image was taken when exposed to 285 nm. The intensity of the sample after LLE was much less compared to the control sample (which did not undergo LLE), as demonstrated in FIG. 21. FIG. 21 shows the change in the fluorescent intensity of the sample after the pDNA extraction. The sample after LLE and the control sample (without undergoing LLE) have the same EtBr concentration. This study demonstrates the successful extraction of DNA with the on-chip LLE process.

On-Chip DNA LLE Quantification for the First Part of this Study

Figure 22:
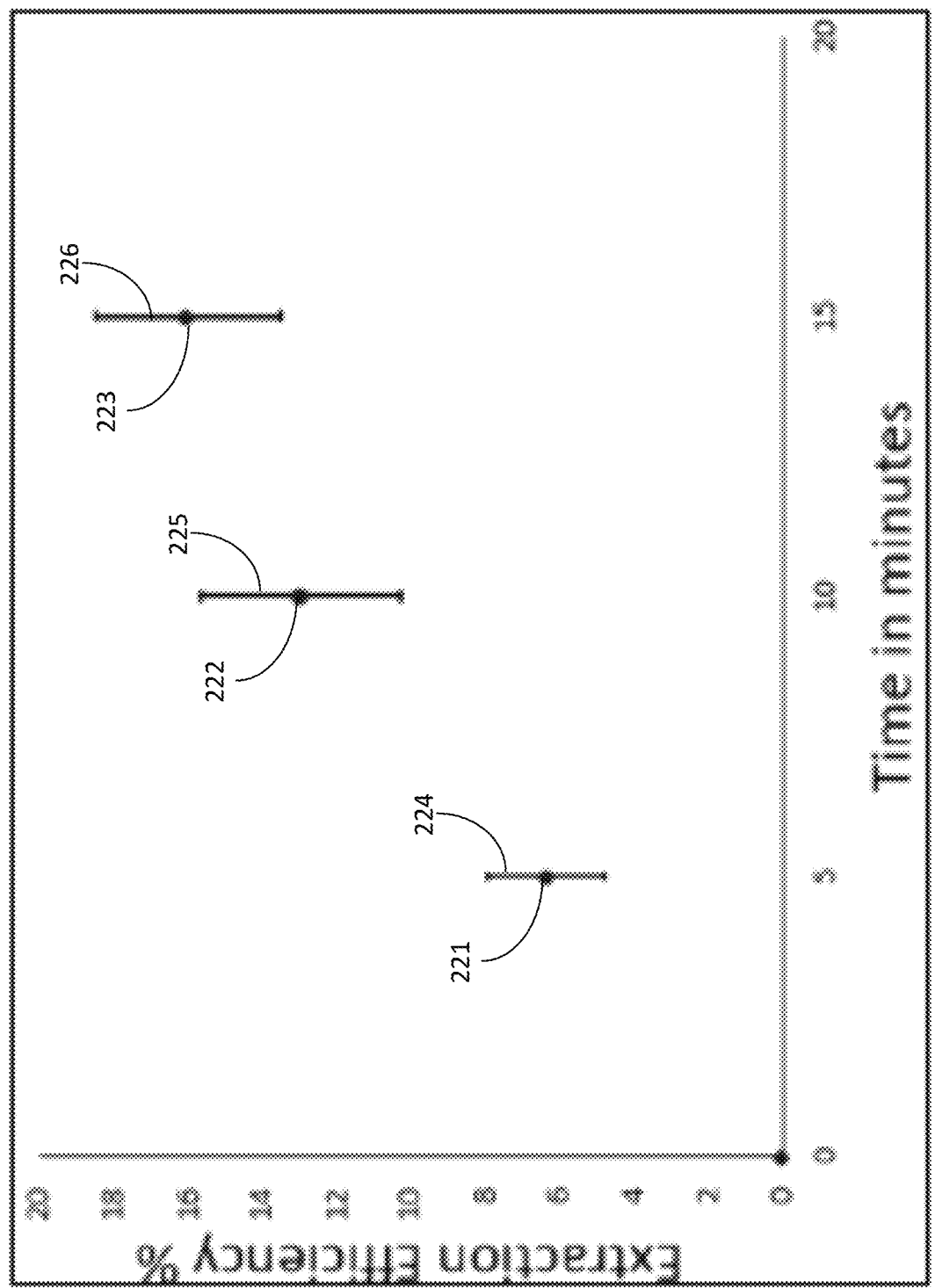
FIG. 22 is a graph showing plots of extraction efficiency of pDNA from the pure pDNA sample for different time durations of LLE using the EWOD device shown in FIG. 5.

LLE tests were performed on the EWOD platform with pure pDNA as the sample in the first part of this study. In the EWOD LLE experiments, 400 nl of pure pDNA droplet and 400 nl of IL droplet were transported onto the mixing region. After the splitting of the phases, the sample droplet was collected and transferred to NanoDrop™ for concentration measurements. The residual DNA concentration in the sample was compared, and the extraction efficiency was calculated. Tests with different extraction times were performed. The results of the first part of this study are plotted in FIG. 22. FIG. 22 is a graph showing plots of extraction efficiency of pDNA from the pure pDNA sample for different time durations of LLE on-chip. The extraction efficiency was plotted against the extraction time of the LLE process, as demonstrated. Experiments were conducted with each of the extraction times of 5, 10, and 15 minutes and the data points were plotted at points 221, 222 and 223, respectively. Error bars 224, 225 and 226 in FIG. 22 indicate the standard deviation using the three data sets.

As can be seen in FIG. 22, the extraction efficiency increases with an increase in the extraction time. Experiments beyond 15 minutes of extraction time can be conducted in a saturated environment condition. In the present experimental setup, a decrease in the volume of the sample due to evaporation was observed beyond 15 minutes of LLE. Therefore, the extraction time was set to an upper limit of 15 minutes. This study demonstrates the successful extraction of pDNA molecules from the sample into the IL phase on the EWOD platform in a DTD format. The IL phase with the extracted DNA molecules can now go for its downstream analysis.

On-Chip DNA Extraction from DNA-Protein Mixture for the Second Part of this Study Results from off-chip and on-chip LLE experiments showed the extraction of pDNA. These results show that BMIM-PF6 can extract pDNA molecules. The results also showed that the IL does not extract BSA protein molecules. As indicated above, the second part of this study was designed to demonstrate the selective extraction of pDNA on the EWOD platform.

The motion of the DNA sample mixed with protein was found to be very sluggish due to surface adsorption of the protein molecules. The surfactant Tween 20 was mixed with the sample to enhance the motion of the droplet. The concentration of the surfactant was maintained the same for all of the experiments. The motion was improved significantly, but still was not the smoothest motion that can be achieved on the EWOD device 20 without protein molecules. Separate studies can be performed to further enhance the sample movability with smart coatings of the top layer on EWOD device 20 and optimizing electrical parameters for droplet motion.

DNA-protein mixture was prepared by adding BSA protein into the pure DNA sample to obtain an equal concentration 100 ng/μl of DNA and protein in the sample. The mixture sample was then dispensed on EWOD device 20 to study the selective DNA extraction in the presence of protein impurities. Since it was confirmed from off-chip experiments that IL does not extract protein molecules, only DNA molecules were quantified for the on-chip experiments. This study demonstrated the effect on DNA extraction in the presence of protein molecules as impurities. Three sets of experiments were conducted for the mixture with an extraction time of 5, 10, and 15 minutes. After the LLE process, the sample was collected and used for DNA concentration measurement following the same procedure as mentioned before. The extraction efficiency of DNA was calculated and was plotted against time in FIG. 23 as points 231, 232 and 233 with corresponding error bars 234, 235 and 236, respectively. For comparison, the previous data from FIG. 22 is also plotted in the same graph.

Figure 23:
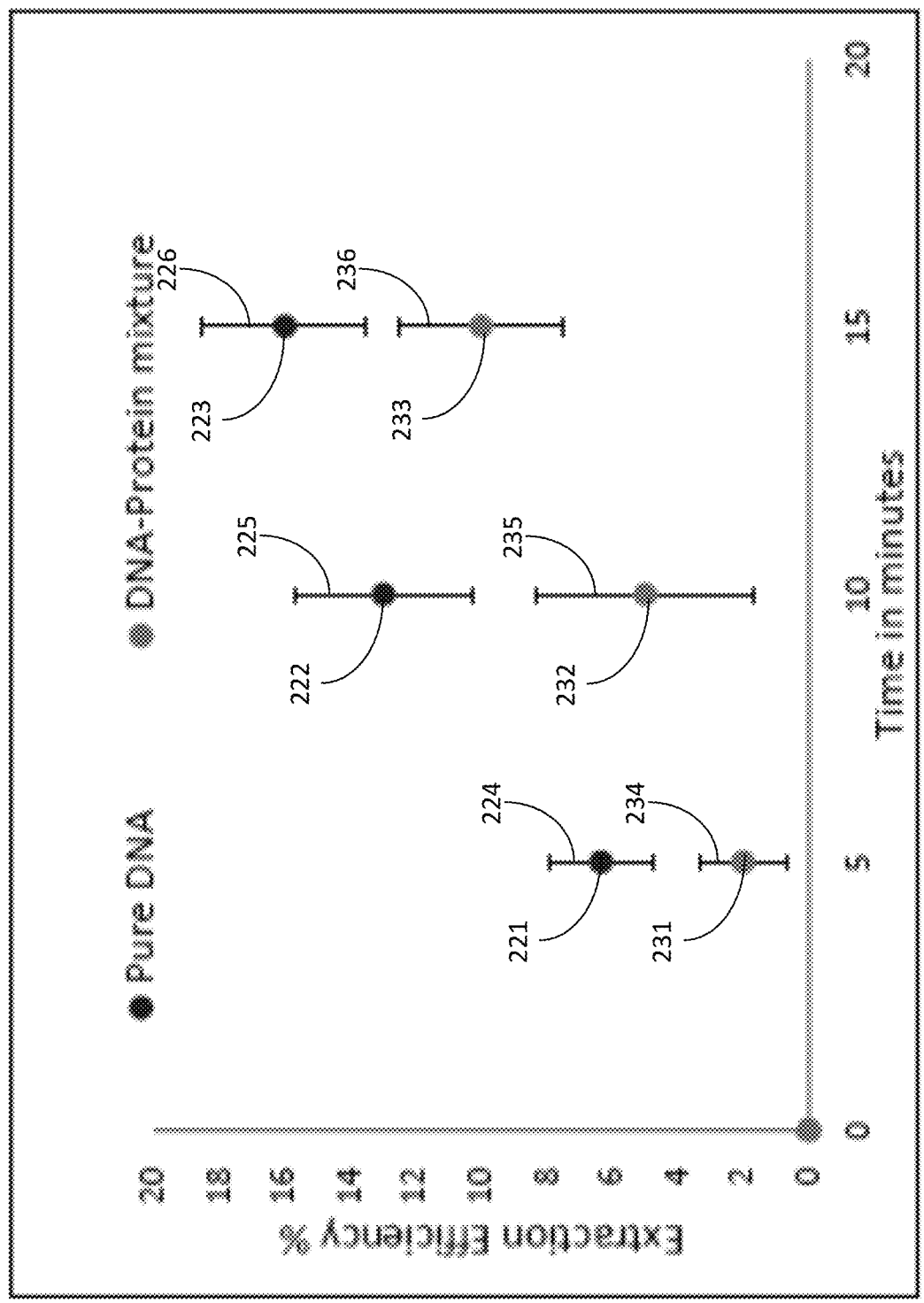
FIG. 23 is a graph of extraction efficiency plotted against time of DNA extracted from a DNA-protein mixture using the EWOD device shown in FIG. 5.

As shown in FIG. 23, the extraction efficiency increases with the extraction time. The decrease in the efficiency of DNA extraction can be attributed to the presence of protein molecules in the sample, which damps the yield of the process. The sluggish motion of the two-phase droplets also contributed to the inferior mixing and, in turn, to the poor extraction yield from the process. As described above, protein co-extraction was not observed with the present liquid-liquid system. Thus, the decrease in the on-chip pDNA extraction in the presence of protein molecules cannot be attributed to protein co-extraction.

Although slightly lower extraction efficiency resulted when impurities (i.e., BSA) are present in the sample (FIG. 23), the result still confirms that the proposed on-chip LLE protocol can selectively isolate DNA from a complex sample solution. The extraction yield can be improved further by designing a liquid-liquid system in which the extractant has a very high affinity for DNA molecules, which is the basis for the third study set forth below. This study demonstrated the integration of DTD DNA LLE enabled by EWOD using IL as the extractant. It provided a microfluidic platform where quick and parallel DNA extractions can be performed in a fully automated fashion.

Conclusions of the Second Study

As the demand for automation and microsystems are on the rise for screening different genes and expressing on different cell lines at high throughput and performing parallel experiments, there is a need for integrating a simple automated protocol of DNA isolation and sample preparation in such systems. A novel microfluidic method of separation of DNA from other impurities such as protein was demonstrated in this work.

In this study, the DNA separates and extracts out preferentially from the sample phase because of its affinity for the IL extractant phase. In the first study, the control sample consisted of pure pDNA. The transfer of pDNA to the IL phase was demonstrated on the EWOD device. On-chip LLE was performed for different extraction times, and the extraction efficiency was found to increase with increasing extraction time. In the second study, protein molecules were added to the control sample as impurities, and selective extraction of pDNA was studied on the EWOD device. It was concluded that protein was not co-extracted in the on-chip LLE process, enabling the selective isolation of DNA for downstream analysis. The method presented in this chapter gets rid of both the use of magnetic beads and the use of an external magnetic field to separate DNA from the sample by enabling LLE in the EWOD microfluidic device. The DNA extraction efficiency can be improved further by having an extractant phase that has a much higher affinity for the target molecules. Compared to standard LLE of DNA in tube-based setups, LLE on EWOD platform fully exploits drop-wise flow control for both sample and extractant phase. The capability of EWOD, when fully exploited, can enable parallel and serial extraction, as well as multiplexing of many different combinatorial extractions on a single chip. Extraction can also be readily performed, providing high-throughput capability if required.

Third Study

On-Chip Aqueous Two-Phase System-Based DNA Extraction Enabled by EWOD Digital Microfluidics.

Aqueous two-phase system (ATPS) is an alternative system for aqueous/organic or aqueous/IL (Aq./IL) extraction media for biomolecule separation. It is a special type of extraction system formed by two aqueous solutions—polymer/polymer (P/P) system or polymer/salt (P/S) system. These systems are known to be efficient for extraction and provide a gentle environment, especially for biomolecules. This study was performed to explore the integration of ATPS-based extraction of DNA on EWOD devices. Two different ATPSs were studied and reported in this study—i) polyethylene glycol/sodium citrate system (PEG/SC) and ii)

polyethylene glycol/ammonium sulfate (PEG/AS) system. The ATPSs in this study were formed off-chip using a conventional method, and the pDNA was introduced to the PEG-rich phase. In the first part of this study, the extraction of pDNA from the PEG-rich phase to the salt-rich phase was studied on-chip. The two droplets of PEG-rich and salt-rich phases were dispensed, merged, mixed, and split on the EWOD chip to complete the aqueous two-phase extraction (ATPE) process. Enhanced efficiency of the DTD extraction of pDNA on EWOD was achieved with the ATPE method, as opposed to the Aq./IL system discussed above in the second study. The extraction studies with each ATPS were performed for various time durations, and the resulting extraction yields were compared. In the second part of this study, BSA protein as interfering molecules was used to show the selective extraction of DNA from the sample mixture. As a demonstration of the screening capability of the EWOD platform to screen different liquid-liquid systems for DNA extraction, the extraction yields of all the systems reported in this disclosure (Aq./IL system and ATPSs) were compared.

Martinus Willem Beijerinck accidentally discovered ATPS by mixing an aqueous solution of gelatin and starch. ATPSs are formed by mixing two polymers of different structures or a polymer and a salt solution. Many other components can be used to form an ATPS, but P/P and P/S systems are the most common. The liquid phases are aqueous in nature, as the name suggests. The process of extraction or mass transfer across the boundary formed by the two phases is known as aqueous two-phase extraction, or ATPE. This form of extraction has several advantages over other traditional methods such as i) these systems are environment-friendly, ii) ease of scale-up and low cost, and iii) they have shown great potential in extracting or separating biomolecules. ATPE method of biomolecule extraction is widely used as a preprocess for concentration and purification of biomolecules such as cell separations, protein purification, DNA/RNA extraction, and enzymes extraction.

Figure 24:
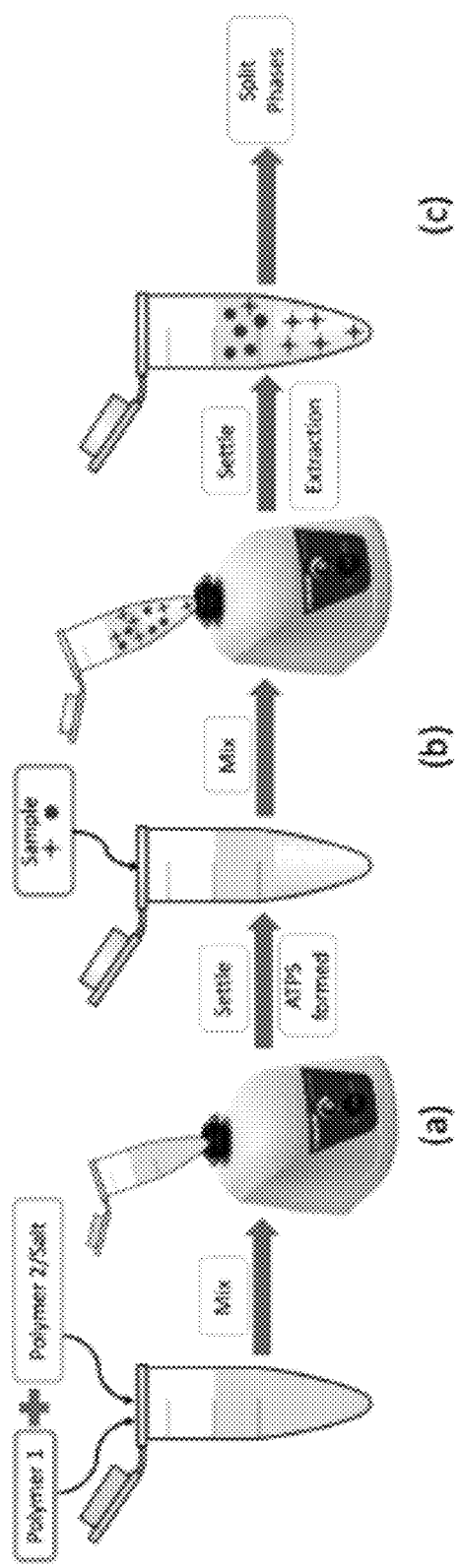
FIG. 24 is a diagram showing the steps of off-chip aqueous two phase extraction (ATPE) process performed in a study of the present disclosure.

In ATPSs, water is the primary solvent, and thus the system forms a very gentle environment for the biomolecules. In standard LLE methods, damage of the biomolecules is inevitable due to the harsh environment created by the organic solvents and other conventional extractant fluids. It has been shown in ATPSs, that the structure and biological activities of the molecules can be retained due to the aqueous nature of the medium, thus allowing relatively fewer degradations. FIG. 24 is a diagram showing the entire process of ATPE, starting from the formation of ATPS and ending with extraction. The two polymers or a polymer and a salt are added, then vortexed to have better mixing, and then left to settle down (step (a) in FIG. 24). This is when the two phases are formed. The sample mixture of different molecules is then added and mixed to have proper distribution along the whole volume (step (b) of FIG. 24). After the solution settles back, the target molecules preferentially separate into one of the phases. The phases are then split, and now the molecules of interest are separated (step (c) of FIG. 24).

The partitioning of biomolecules in ATPS is mainly decided by the factors—hydrostatic and electrostatic interactions, the specific affinity of molecules, molecular size, and conformation. ATPSs are mostly optimized by varying several variables, such as physicochemical properties (e.g., molecular weight of polymer), pH, and temperature of the ATPS. The optimization of these variables can be very laborious and may consume many reagents. There could be tremendous advancement with miniaturization and automation of ATPS-based partition studies, with the ease of user-defined automated variables optimizations.

Attempts have been made to perform ATPE in microscale with the help of microfluidics. Most of these attempts are made in continuous microfluidics. These systems suffer from the drawback of limited mixing capabilities and extraction time, and imperfect phase splitting at the end of the process. In most of the microsystems, ATPS is performed off-chip, and only the ATPE can be performed on-chip. Attempts have been made to study ATPE of different biomolecules in the microscale, but very few studies have been performed for ATPE of DNA molecules. The integration of the ATPE process for DNA molecules in the microscale could lead to a one-step solution for enriching the sample for the downstream nucleic acid assays. Due to the aqueous nature of the extractant phase, the sample can directly go for the next step in the workflow.

The formation of ATPS on EWOD DMF, and the ATPE of dye molecules has been demonstrated in the past. The present study, however, is the first attempt to demonstrate the ATPE of DNA from a sample using two ATPSs on EWOD. Several research groups are actively investigating IL as an extractant for DNA isolation, as was studied in the second study discussed above. However, the DNA extracted by IL needs a buffer exchange step as most of the downstream nucleic acid assays are still done in the aqueous media. In contrast, the extractant phase in ATPS being aqueous can directly go to the downstream assays. In the present study, two ATPSs were studied for DNA extraction on the EWOD device 20. One ATPS consisted of PEG/SC, and the other ATPS consisted of PEG/AS. After the ATPE, the DNA was found to be concentrated in the salt-rich phase. The phases were split, and the salt-rich phase was acquired for DNA concentration measurement. Unlike in the second study in which the DNA LLE was quantified by an indirect method by measuring the residual DNA concentration in the sample, in the present study, the extracted DNA was quantified directly in the extractant phase. In a first part of the present study, on-chip ATPE was investigated, introducing pDNA in the PEG-rich phase (formed off-chip) with no other impurities present. The extraction yield for the ATPS using PEG/SC was found to be higher than that of the ATPS using PEG/AS. In a second part of the present study, BSA protein molecules were spiked in the PEG-rich phase along with the pDNA molecules to study the selective extraction of pDNA from the mixture. The pDNA extraction yields were found again to be higher for the PEG/SC ATPS than for the PEG/AS ATPS. However, co-extraction of protein was also observed along with the pDNA molecules with both of the ATPSs. The protein co-extraction was found to be quite significant for the PEG/SC ATPS. Thus, the PEG/AS ATPS showed greater selectivity for pDNA extraction, resulting in purer final pDNA product in the salt-rich phase.

Experimental

Chemicals

PEG (molar mass 600 g/mol), AS (molar mass 132.14 g/mol), and SC (molar mass 258.06 g/mol) were purchased from ACROS Organics, Fisher Scientific and Sigma life science, respectively. To obtain a particular polymer/salt (P/S) ATPS, pure solutions of PEG and AS or SC were mixed at designated concentrations. Altogether, two different ATPSs were formed to study the partition of pDNA in these systems. The ATPSs and their composition were selected by observing the biphasic curves. Biphasic curves indicate the threshold concentrations beyond which the resultant solution will separate into two phases.

For the DNA extraction part of the present study, the same pDNA pVAX1-hVEGF165 transformed in growth strain DH5-Alpha, was used as in the second study discussed above. The bacterial strain was cultured to increase the colony, and from the expanded colony, the plasmid DNA was extracted using the Qiagen Hispeed kit. The pure pDNA sample mixed in the PEG-rich phase was used for all of the controlled ATPE experiments. The details of the plasmid production steps were discussed above in the second study. BSA protein was used as the impurity molecules to show the selective extraction of DNA from a mixture of DNA and protein.

Fabrication and Device Design

The device design and the fabrication steps are the same as those described above in the first and second studies.

ATPS Formation

The two ATPSs used for pDNA partition study were prepared off-chip by mixing appropriate amounts of PEG solution and the salt in water, as shown in step (a) of FIG. 24. The final composition of the ATPS prepared was 22% (w/w) PEG and 17% (w/w) of the salt. The systems were homogenized by vortexing for 5 minutes and then centrifuged at 4000 rpm for 5 minutes. The two aqueous phases were formed, and they were split very carefully. Pure pDNA was added to the PEG-rich phase, and concentration was adjusted to 100 ng/µl and vortexed for proper mixing. The PEG-rich phase with the pDNA and the salt-rich phase were stored for the ATPE experiments. Now, the PEG-rich phase has the pDNA, and the extraction of pDNA from PEG to the salt-rich phase was studied both on the EWOD device 20 and off-chip.

Off-Chip pDNA Extraction

The DNA extraction was first studied off-chip using the ATPS formed as described above. The PEG-rich phase containing the pDNA molecules was mixed with the salt-rich phase and vortex for 5 minutes. Here, the salt-rich phase acts as the extractant phase. The mixture was left to settle back to form the two phases. The phases were then very carefully split, and the bottom salt-rich phase was transferred for spectrophotometric based DNA concentration measurement. The presence of pDNA in the salt-phase confirmed the successful extraction of pDNA by the ATPS in off-chip experiments.

Separate experiments were conducted where BSA protein molecules were spiked into the PEG-rich phase to form a mixture of pDNA and protein. The same procedure of mixing and splitting the two phases was carried out. The salt-rich bottom phase was then analyzed for both pDNA and protein concentration.

On-Chip pDNA Extraction

Figure 25:
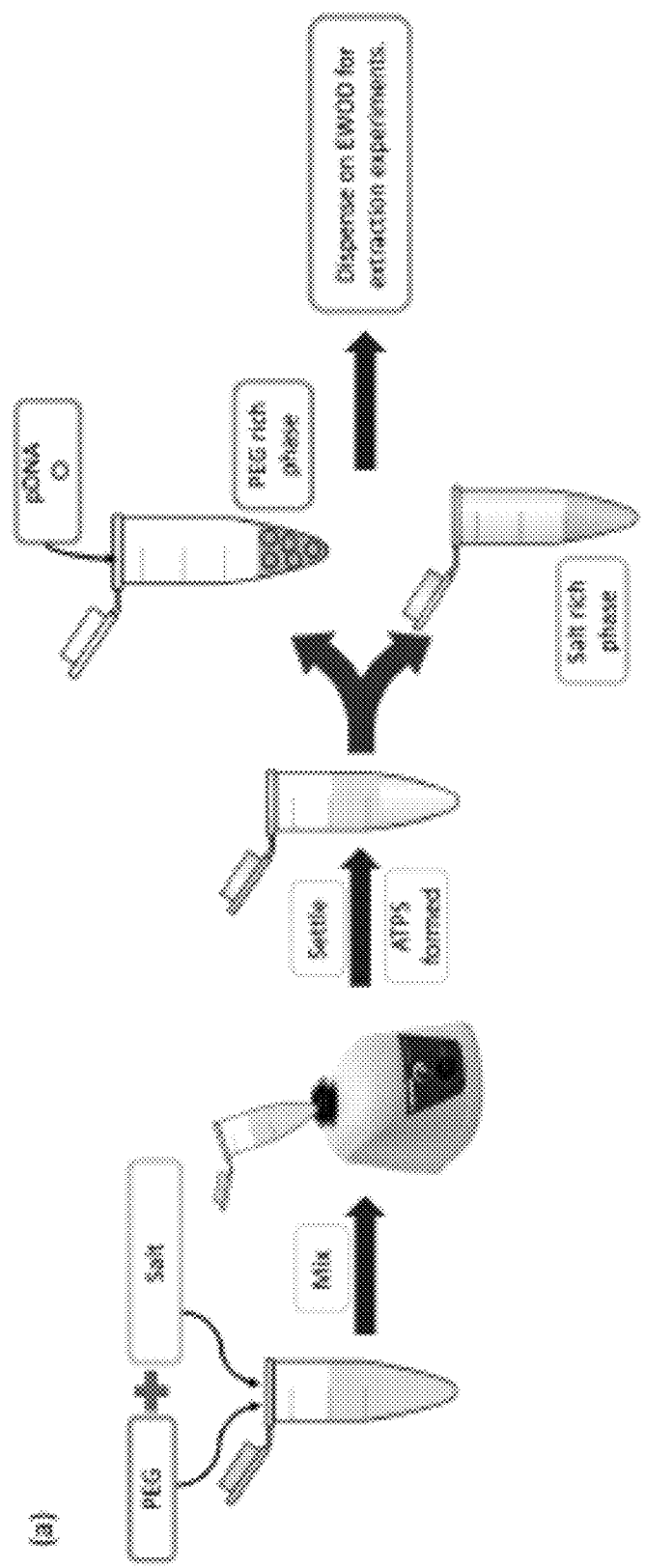
FIG. 25 is a diagram showing the steps of off-chip aqueous two phase system (ATPS) formation performed in a study of the present disclosure.
Figure 26:
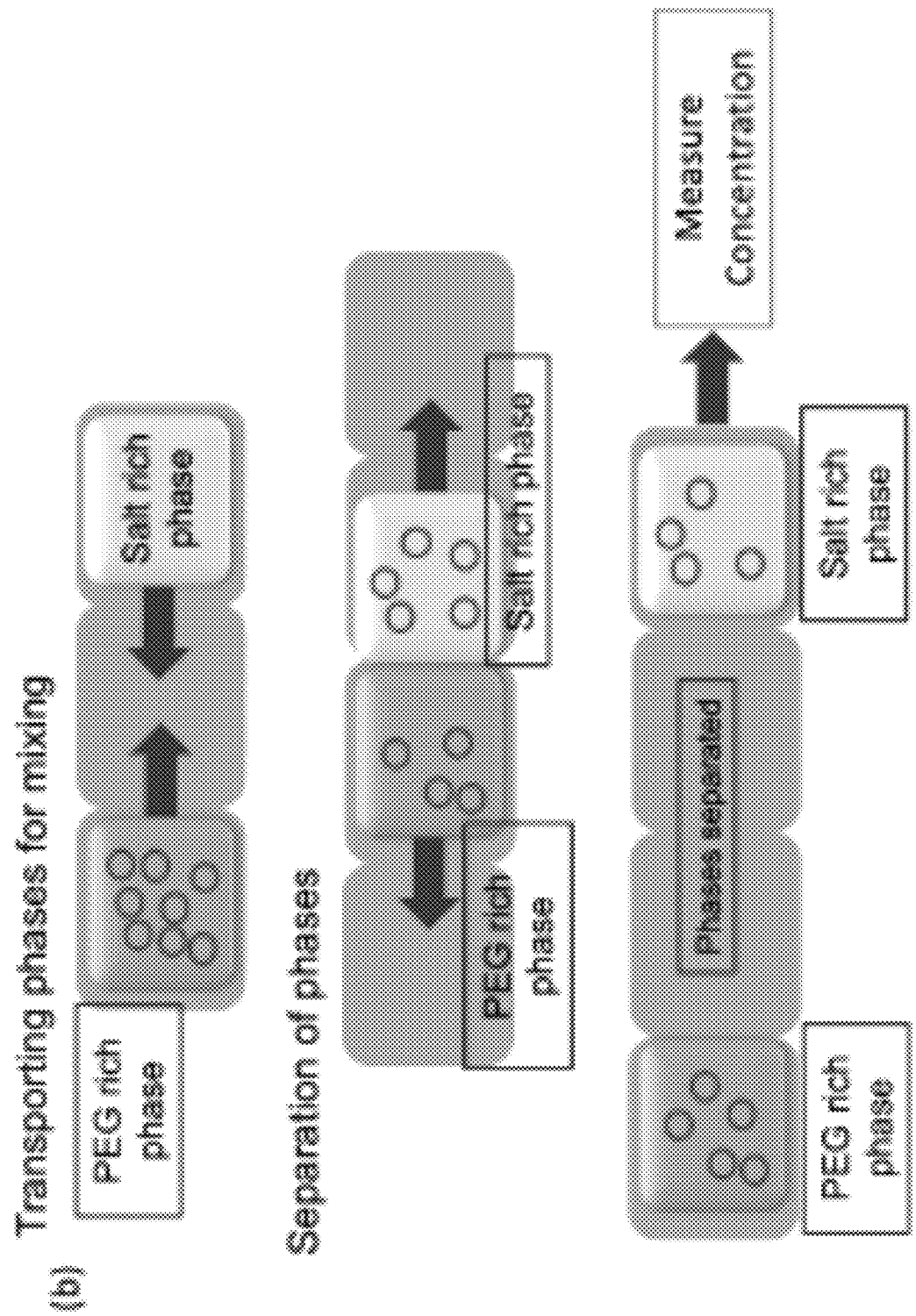
FIG. 26 is a diagram illustrating an ATPE protocol performed by the EWOD device shown in FIG. 5 in accordance with an embodiment.

The ATPS formed off-chip was used to demonstrate the ATPE process on the EWOD device. FIG. 25 is a diagram illustrating the steps of off-chip ATPS formation in accordance with an embodiment. The PEG-rich phase containing pDNA, and the salt-rich phase were loaded on separate reservoirs of the EWOD device 20. FIG. 26 is a diagram illustrating the entire on-chip ATPE protocol in accordance with an embodiment. The initial concentration of pDNA in the PEG-rich phase was adjusted to 100 ng/µl. Two droplets of equal volume were dispensed from each reservoir by operating the EWOD device 20 in the manner described above. The droplets were moved with the EWOD electrodes and were brought into contact, at which point the extraction begins. The merged liquid droplets were mixed by moving them in a particular fashion. The most optimized on-chip mixing scheme from the previous study was adopted to have the maximum extraction of pDNA from the PEG-rich phase to the salt-rich phase.

The end step of the process is to split the phases using the forces of the EWOD device 20, and the extractant droplet with the isolated pDNA is suitable for its downstream analysis. The phase splitting was achieved on-chip by driving the two phases onto two separate opposite electrodes and applying EWOD forces at opposite ends to split the phases at the interface. The salt-rich phase was analyzed for DNA concentration measurement to quantify the ATPE process on-chip. ATPE experiments were conducted for both of the ATPSs, and results were compared to find a system with a higher extraction yield. Protein molecules were spiked into the PEG-rich phase to show the selectivity of on-chip pDNA extraction in a separate study. The concentration of pDNA and BSA in these experiments were adjusted to an equal concentration of 100 ng/µl.

Extraction Quantification

The DNA extraction quantification for both on-chip and off-chip studies were performed by using the aforementioned NanoDrop™ instrument. After the extraction process, the salt-rich phase was collected and transferred to NanoDrop™ instrument for concentration measurements. The DNA concentration measurement was done at 260 nm wavelength. The presence of pDNA in the salt confirmed the success of the ATPE process. Due to the aqueous nature of the extractant (salt-rich phase), it was compatible with the NanoDrop™ instrument, and hence, the direct quantitation of the extractant phase was possible. This was not the case with the second study discussed above, where the extractant (IL) phase was not compatible with the NanoDrop™ instrument. For the protein quantification, the salt-rich phase was measured at 280 nm wavelength in the NanoDrop™ instrument. The blank used in all the measurements consisted of the initial salt-rich phase obtained from ATPS, but without the pDNA or BSA molecules.

Results and Discussion

Off-Chip DNA Extraction

Figure 27B:
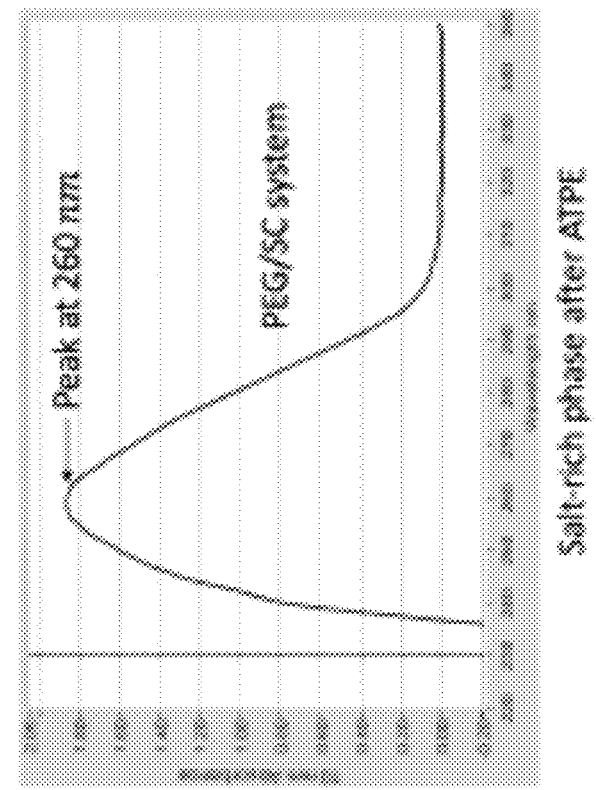
FIGS. 27A and 27B are graphs of the absorbance as a function of wavelength for a PEG/SC ATPS before and after ATPE, respectively.
Figure 27A:
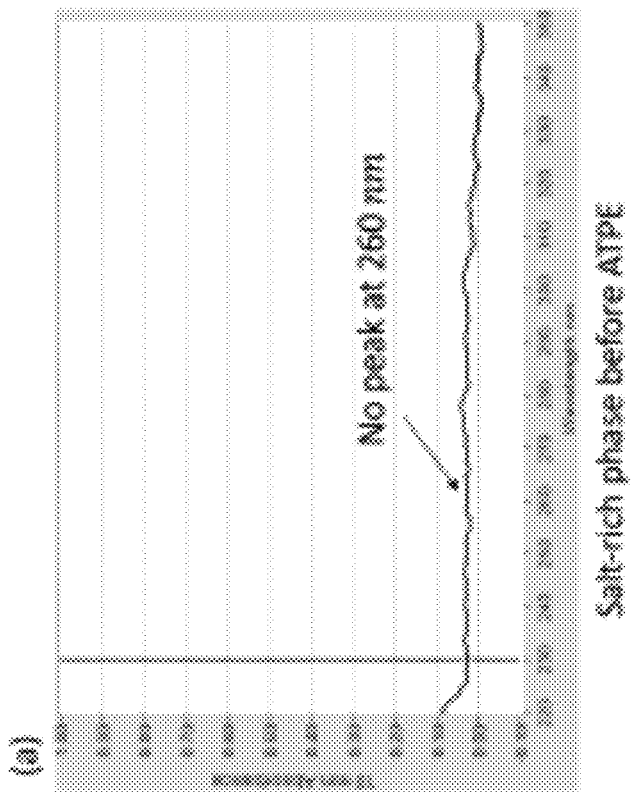
Figures 28A, 28B:
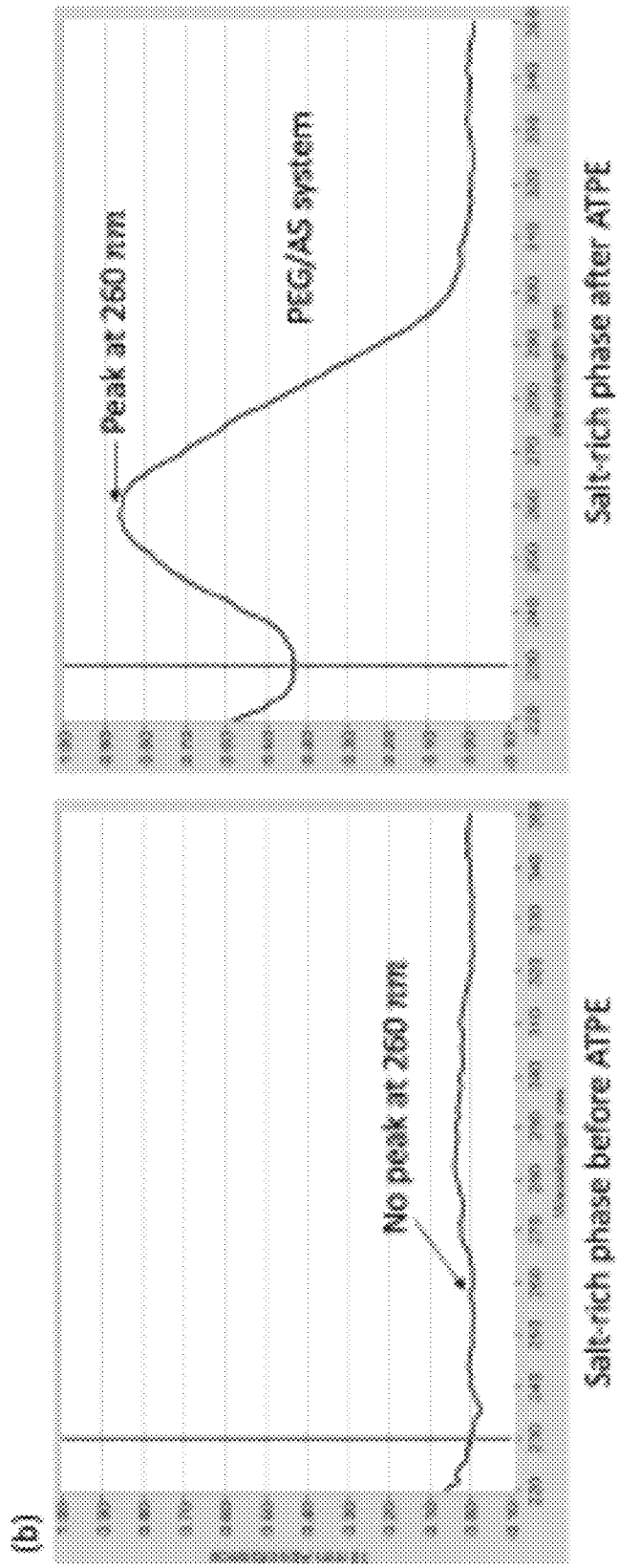
FIGS. 28A and 28B are graphs of the absorbance as a function of wavelength for a PEG/AS ATPS before and after ATPE, respectively.

The pDNA concentration in the salt-rich phase was measured from the off-chip ATPE experiments. Experiments were performed with both of the ATPSs. FIGS. 27A and 27B are graphs of the absorbance as a function of wavelength for the PEG/SC ATPS before and after ATPE, respectively. FIGS. 28A and 28B are graphs of the absorbance as a function of wavelength for the PEG/AS ATPS before and after ATPE, respectively. It can be seen in FIGS. 27B and 28B that there are peaks in absorbance for both of the ATPSs 260 nm in the salt-rich phase due to the presence of pDNA. The salt-rich phase from the PEG/SC ATPS was analyzed in the NanoDrop™ instrument, and the absorbance measurements are shown in FIGS. 27A and 27B. The total partitioning resulted in a 90% extraction of pDNA. FIG. 27A shows no peak at the 260 nm wavelength for the salt-rich phase before the ATPE experiment was conducted, whereas FIG. 27B shows a sharp peak at the 260 nm wavelength after the ATPE experiment. With reference to FIGS. 28A and 28B, the PEG/AS system extraction resulted in an extraction efficiency of almost 70%. There was again no peak observed before the ATPE (FIG. 28A), and a sharp peak at the 260 nm wavelength was observed after the extraction process (FIG. 28B). The presence of pDNA in the salt-rich phase in both systems confirmed the successful extraction of pDNA by the ATPSs. Thus, the two ATPSs are suitable for studying the pDNA extraction on the EWOD platform.

ATPE of pDNA on the EWOD Device

Figures 29A, 29B, 29C, 29D, 29E:
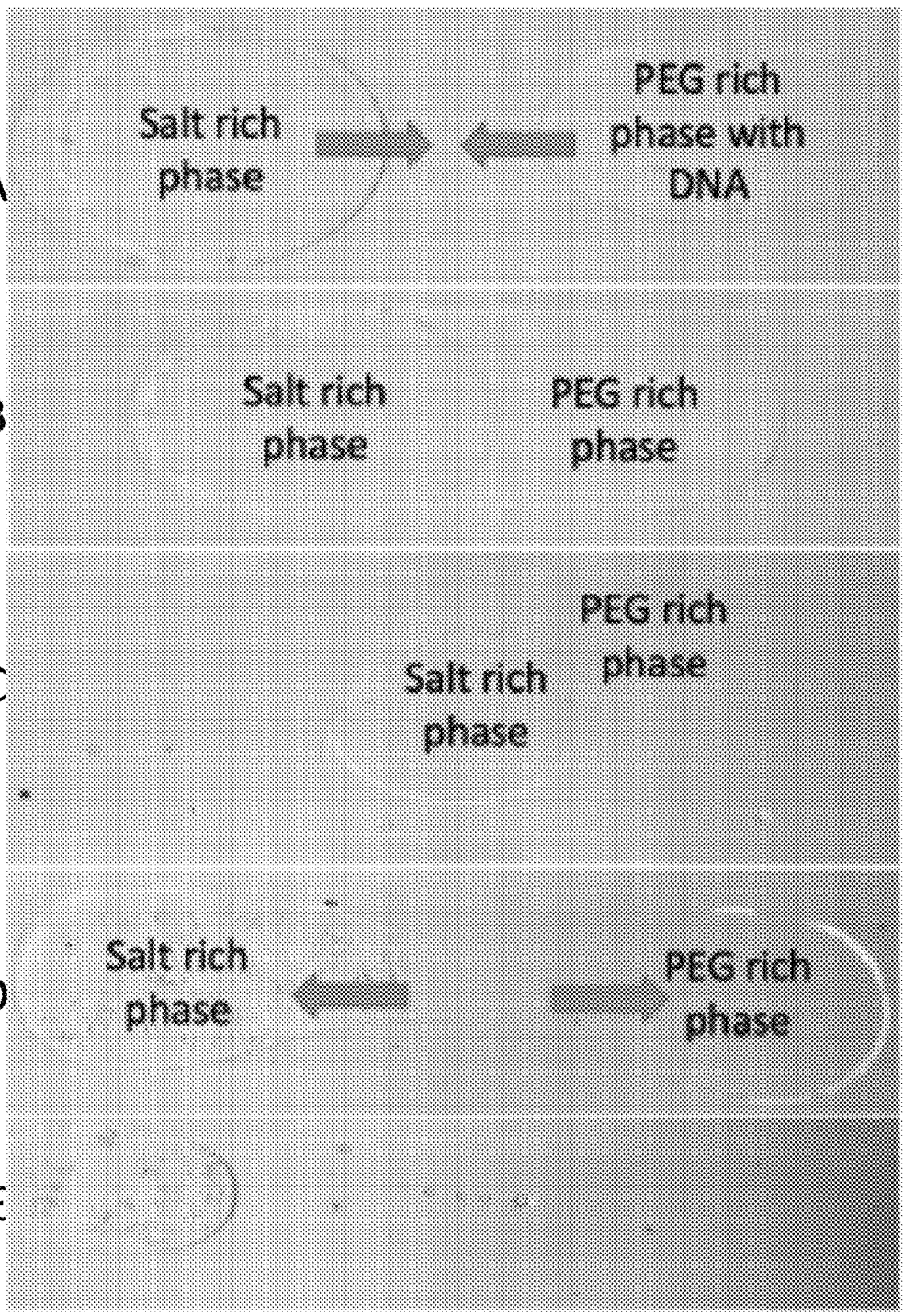
FIGS. 29A-29E are snapshots from an experiment of an entire protocol for ATPE of pDNA on the EWOD device shown in FIG. 5 in accordance with a representative embodiment.

FIGS. 29A-29E are snapshots from the experiment of the entire protocol for ATPE of pDNA on the EWOD device 20 in accordance with a representative embodiment. In FIG. 29A, the salt-rich phase and the PEG-rich phase are merged. In FIG. 29B, DNA extraction takes place along the interface of the phases. In FIG. 29C, the phases are moved around to enhance mixing and extraction. In FIG. 29D, the phases are split to conclude ATPE. In FIG. 29E, the salt-rich phase is collected for concentration measurement using the Nano-Drop™ instrument.

The EWOD device 20 was successful in generating the PEG-rich phase with the pDNA molecules, and the salt-rich phase droplets of equal volume, transporting the droplets to the mixing and extraction zone, and finally splitting the two phases to complete the ATPE process. The optimized mixing, as described above in the second study, was adopted for all the experiments. Similar to the second study, it was observed that the droplet, which was easy to actuate with EWOD forces, would engulf the other phase. In the present study, the PEG-rich phase was more mobile than the salt-rich phase under the voltage application, and hence, completely engulfed the latter phase. During mixing, in this study, the salt-rich phase was kept stationary, and the PEG-rich phase was made to rotate around. After the splitting of the phases, the salt-rich phase droplet was collected for concentration measurement. The volume of the salt-rich phase droplet retrieved from the EWOD device 20 after the ATPE process was ~400-500 nl. The individual droplet volume from each experiment was too small for multiple concentration measurements in the NanoDrop™ instrument. Thus, three similar experiments were conducted, and the droplets from each experiment were collected. The combined volume from the three experiments was then used for the concentration measurements. The obtained measurement thus corresponds to one average data set (from three tests) for an experimental condition. Three similar sets of experiments were conducted to obtain three data sets, each consisting of three experimental repeats. Thus, the error bars in each of the following studies indicate standard deviation using a total of nine experimental repeats.

Figure 30:
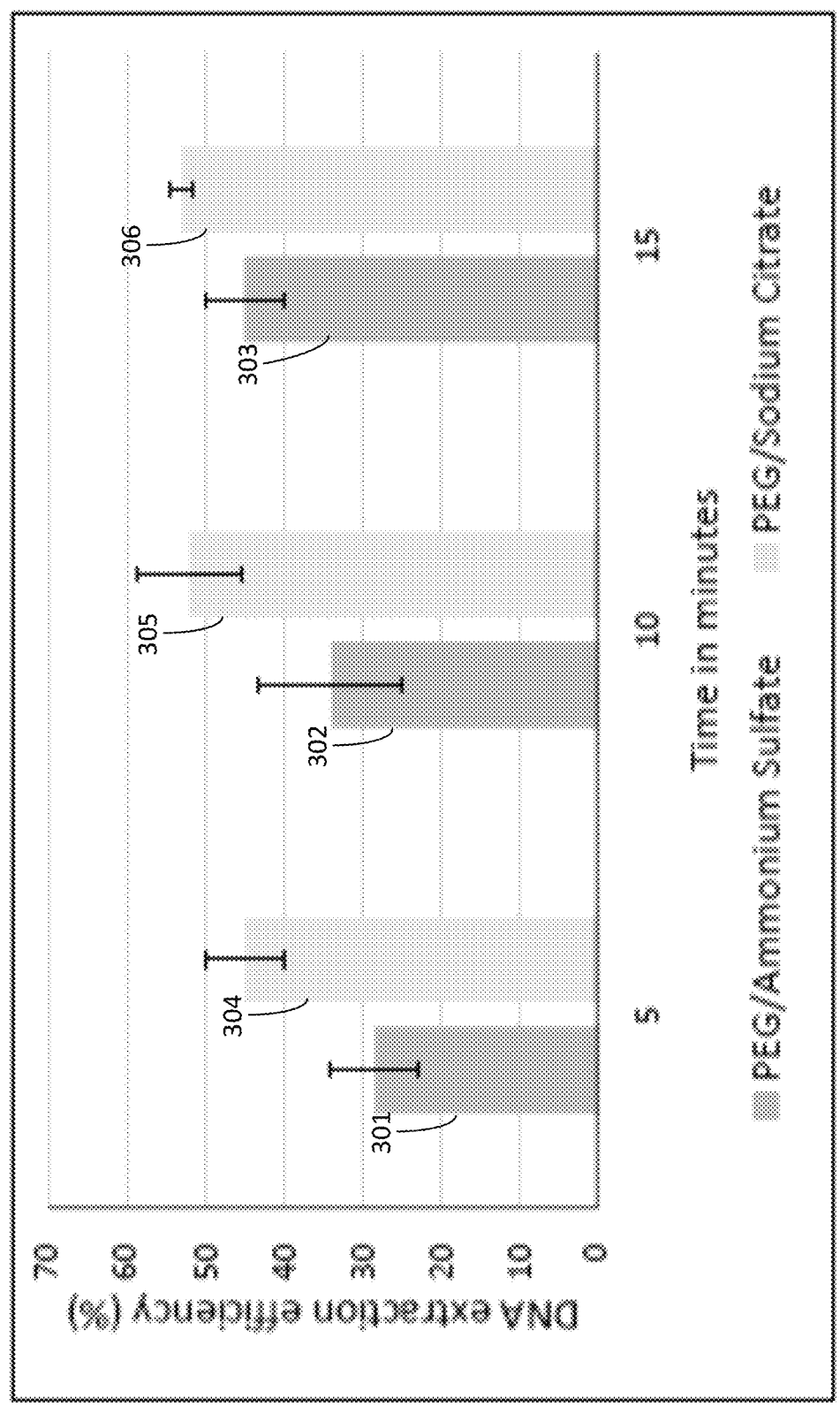
FIG. 30 is a bar graph that shows extraction efficiency plotted against the extraction time for results of an ATPE process performed on the EWOD device shown in FIG. 5 using two different ATPSs.

In the first ATPE experiment study on the EWOD device 20, the PEG-rich phase contained only pDNA molecules to demonstrate the transfer of DNA molecules using ATPS. The results from the off-chip experiments discussed above with reference to FIGS. 27A-28B showed the successful extraction of pDNA with the two ATPSs. ATPE experiments were performed on the EWOD device 20 to demonstrate DTD format extraction. Experiments were performed by varying the extraction time at 5, 10, and 15 minutes. FIG. 30 is a bar graph that shows the results of the on-chip ATPE process for both of the ATPSs in terms of the extraction efficiency plotted against the extraction time. The extraction efficiency was calculated by finding the difference in the salt-rich phase pDNA concentration before and after the process. The bars 301, 302 and 303 correspond to the PEG/AS ATPS and the bars 304, 305 and 306 correspond to the PEG/SC ATPS.

FIG. 30 illustrates the extraction efficiency obtained from the two ATPSs for different time periods of mixing. The bars 301-303 show the efficiency obtained with the PEG/AS system, and the bars 304-306 show the efficiency obtained with the PEG/SC system. As can be seen, in FIG. 30, the extraction efficiency increases with the increase in the extraction time. Experiments beyond 15 minutes of extraction time can be conducted in a saturated environment condition. In this experimental setup, a decrease in the volume of the droplets was observed (as was seen in the previous studies) due to evaporation beyond 15 minutes. So, the extraction time was set to an upper limit of 15 minutes in the present test setup. As can be seen in FIG. 30, the ATPE with the PEG/SC system shows a higher yield of pDNA extraction than that by the PEG/AS system. Also to be noted here, the extraction yield from these systems is higher compared to that obtained from the Aq./IL system, as was reported in the second study discussed above.

On-Chip pDNA Extraction from pDNA-Protein Mixture

Figure 31:
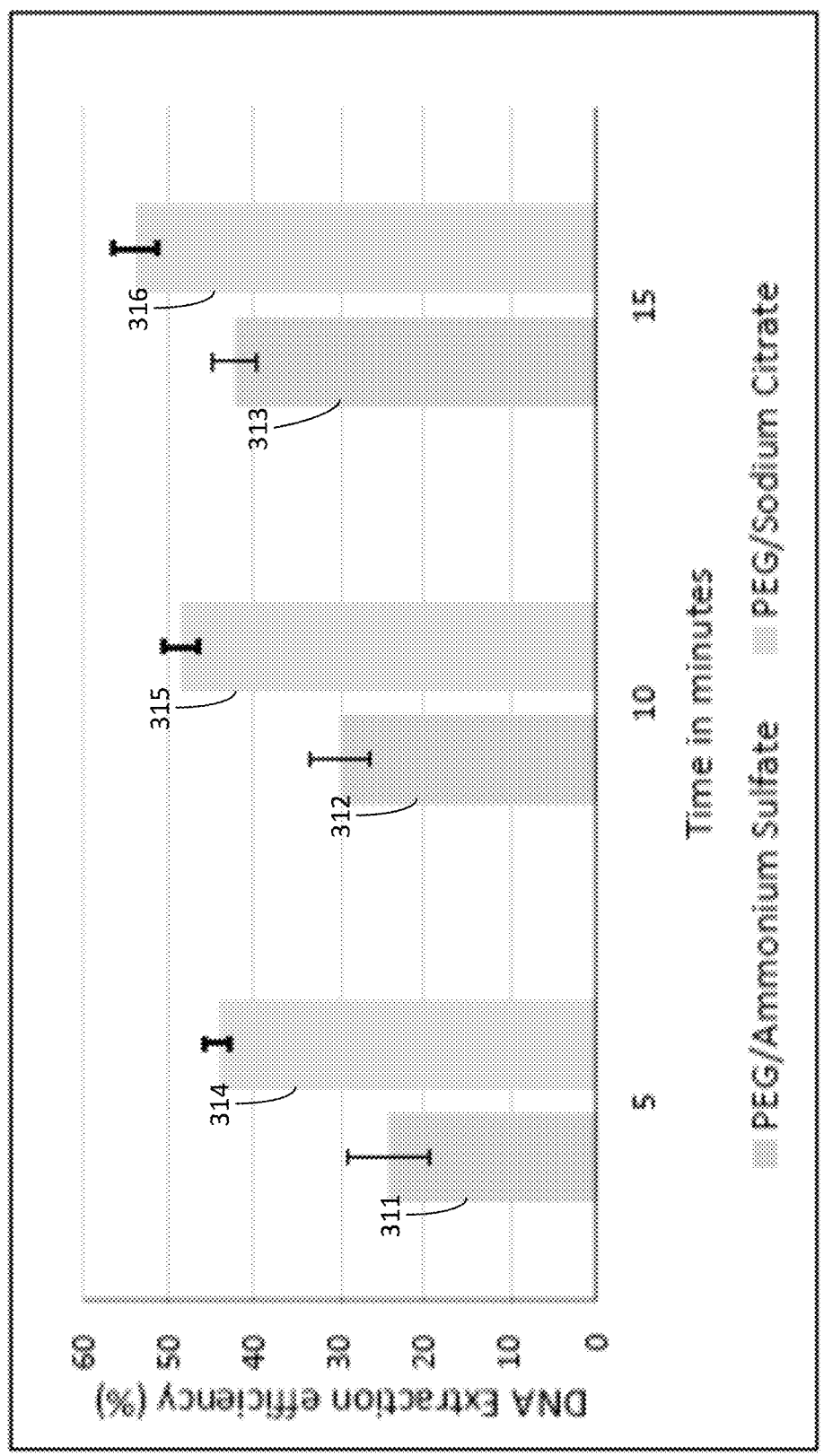
FIG. 31 is a bar graph that shows the extraction efficiency plotted against the extraction time for the ATPE process performed on the EWOD device shown in FIG. 5 for two ATPSs for pDNA extraction from the pDNA-protein mixture.

In the second part of the present study, the ATPE performance of the two ATPS with interfering protein BSA molecules was conducted by adding protein to the PEG-rich phase. The control PEG-rich phase now has both the pDNA and the BSA molecules. The same procedure discussed above was done for the on-chip ATPE process in this part of the study. A droplet of the PEG-rich phase containing pDNA and protein and a droplet of salt-rich phase were introduced to the EWOD device 20. The two droplets were merged, and after proper mixing, they were split. The salt-rich phase was transferred for both DNA and protein quantification. FIG. 31 is a bar graph that shows the results of the on-chip ATPE process for both of the ATPSs in terms of the extraction efficiency plotted against the extraction time for pDNA extraction from the pDNA-protein mixture. FIG. 31 shows the DNA extraction efficiency with protein spiked as an impurity. The bars 311, 312 and 313 correspond to the PEG/AS ATPS and the bars 314, 315 and 316 correspond to the PEG/SC ATPS.

The same trend that was observed from the results of the experiments shown in FIG. 30 is also seen here. The PEG/SC system (bars 314, 315 and 316) results in a higher extraction yield compared to PEG/AS system (bars 311, 312 and 313). Not much decrease in DNA extraction efficiency (from the study in FIG. 30) in the presence of protein was observed, as was the case with the Aq./IL system. The droplet motion was smooth in the case of ATPS on the EWOD platform upon the addition of the surfactant Tween 20. Due to the ease of the movement of the ATPS droplets, it was possible to replicate the exact optimized mixing scheme described above in the second study. It was observed that the response of the ATPS to EWOD actuation was better compared to the Aq./IL, system (reported in the second study).

Figure 32:
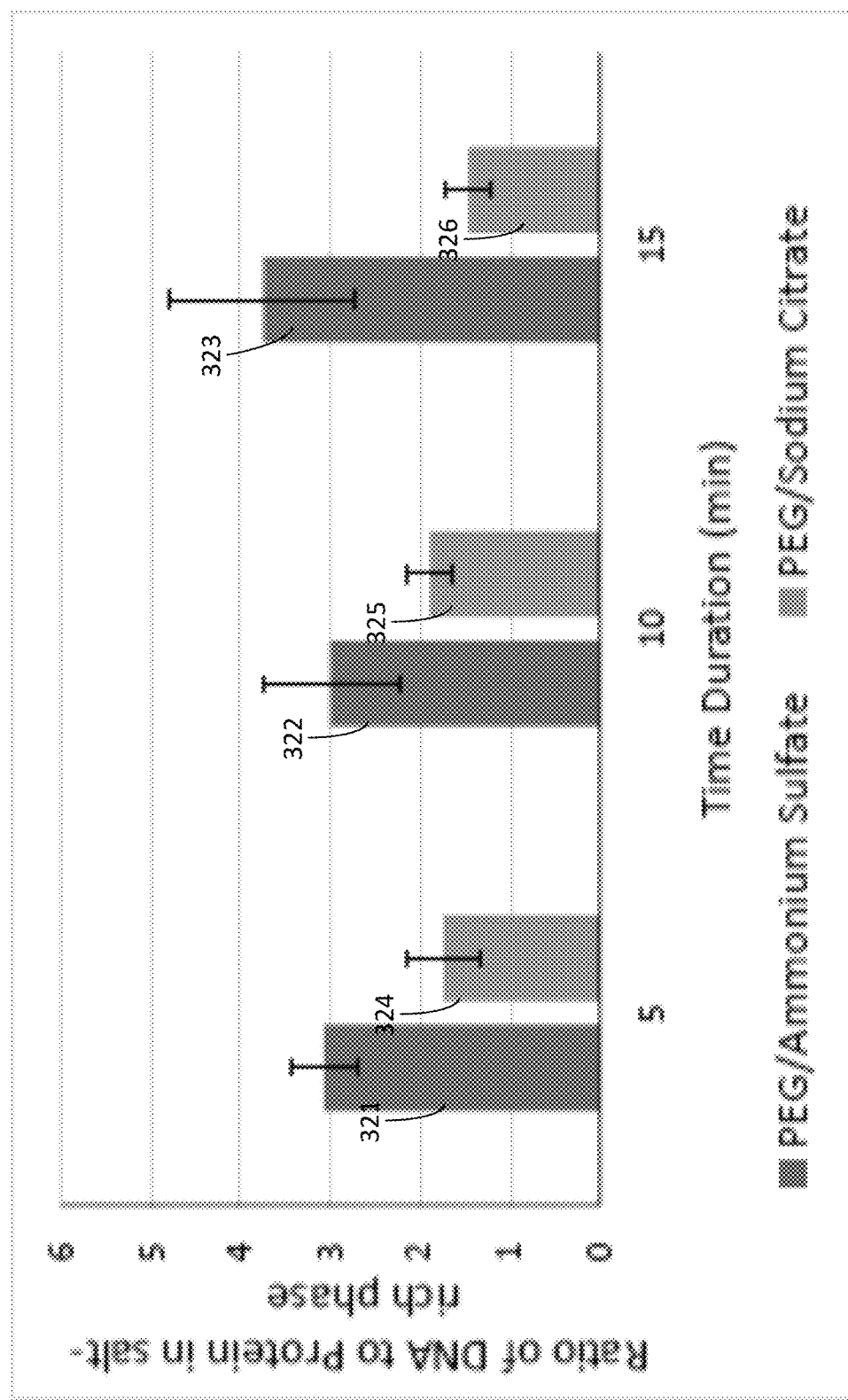
FIG. 32 is a bar graph that shows the ratio of DNA to protein in salt-rich phase plotted against the extraction time for the ATPE process performed on the EWOD device shown in FIG. 5 for two ATPSs.

The protein co-extraction was quantified by measuring the protein content in the salt-rich phase with NanoDrop™. It was found that with the PEG/AS system, the protein co-extraction was less, leading to much pure pDNA in the salt-rich phase than the PEG/SC system. Although the on-chip pDNA extraction with PEG/SC was high, the high protein co-extraction makes it less selective to pDNA extraction in the presence of other impurities (protein). The protein co-extraction by the salt-rich phase can be attributed to the pH of the system. The pH of the two systems in this study was found to be in the range of 6.8-6.9 for all the experiments, which can induce a negative charge on the BSA protein molecules (isoelectric point of BSA is 4.8). The negative charge of the BSA molecules could be a factor for the electrostatic interaction with the positive components of the salt-rich phase, which causes the co-extraction. The ratio of the DNA to protein extraction results for the two systems are plotted in FIG. 32. FIG. 32 is a bar graph that shows the results of the on-chip ATPE process for both of the ATPSs in terms of the ratio of DNA to protein in salt-rich phase plotted against the extraction time for DNA extraction efficiency with protein spiked as an impurity. The bars 321, 322 and 323 correspond to the PEG/AS ATPS and the bars 324, 325 and 326 correspond to the PEG/SC ATPS.

The bars 321-323 representing the PEG/AS system indicate the increase in the ratio of DNA to protein extracted over time and that the ratio is higher than that indicated by the bars 324-326 representing the PEG/SC system. The orange bar decreases with time as more protein molecules are also co-extracted with more extended extraction experiments, thus decreasing the purity of the final extracted pDNA. Hence, from these experiments, the PEG/AS system was found to be a better choice among the two ATPSs. As mentioned above, in future experiments, the pH of the system can be adjusted to study the effect on protein co-extraction.

Effect of Initial pDNA Concentration

Figure 33:
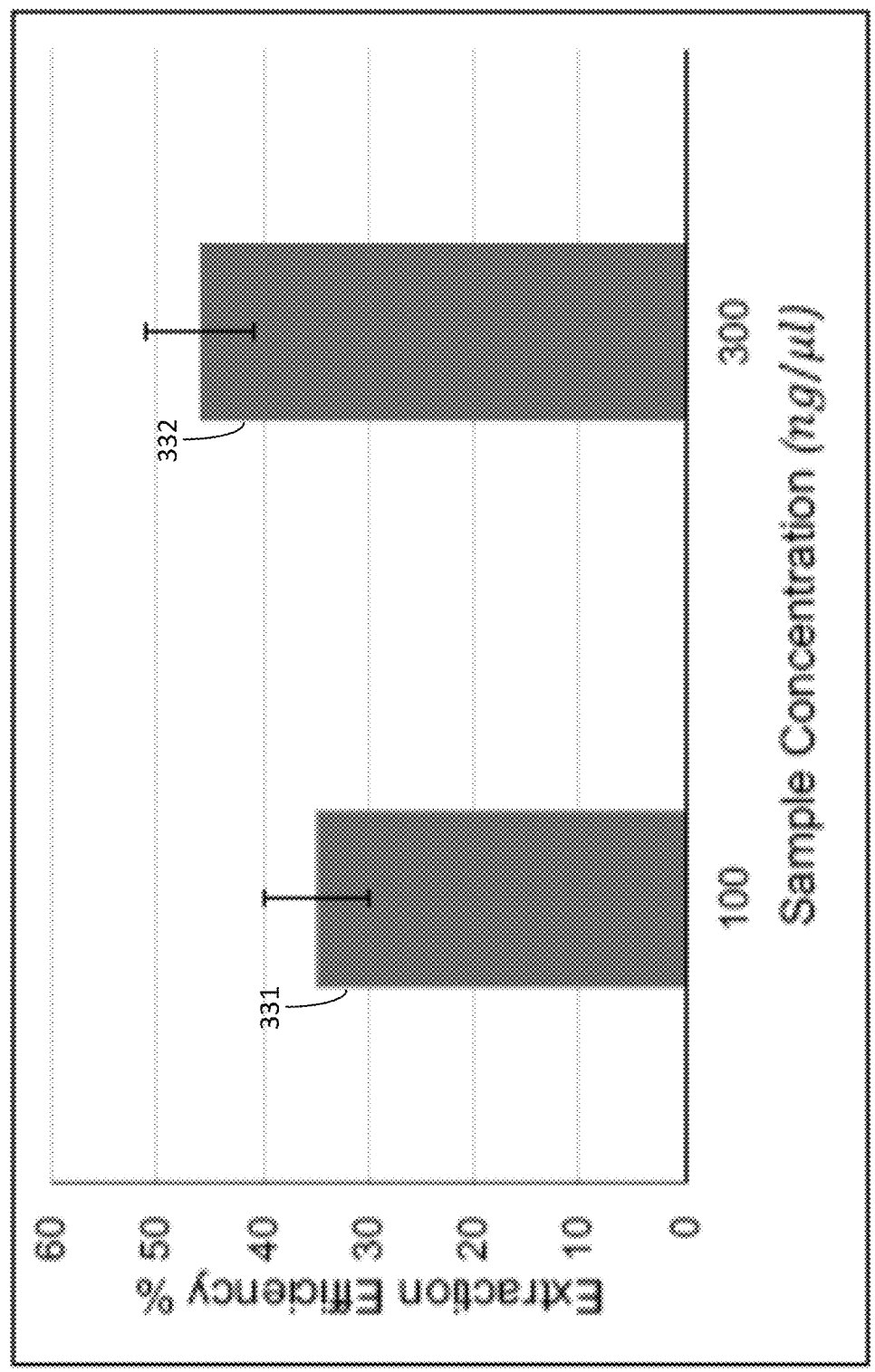
FIG. 33 is a bar graph of extraction efficiency plotted against sample concentration using a PEG/AS ATPS for different initial pDNA concentrations in PEG-rich phase and a constant extraction time of 10 minutes.

For all the tests discussed so far, the initial pDNA concentration in the PEG-rich phase was kept at 100 ng/µl. The extraction efficiency of 35% was achieved with the PEG/AS system when the extraction is done for 10 minutes (FIG. 30). However, if the initial pDNA (or lysate load, when the starting sample is cells) concentration is high, it can give the same extraction yield in a short period of extraction time. This study was performed to determine the effect of initial pDNA concentration in the extraction rate, where the extraction time was kept constant at 10 minutes. The PEG/AS system was used for this study, and the PEG-rich phase contained only pDNA molecules. Sets of experiments were done with two initial pDNA concentrations in the PEG-rich phase: 100 ng/µl and 300 ng/µl). The results of this study are plotted in the bar graph shown in FIG. 33. FIG. 33 is a bar graph of extraction efficiency plotted against sample concentration using the PEG/AS system for different initial pDNA concentrations in the PEG-rich phase and a constant extraction time of 10 minutes. With 300 ng/µl initial pDNA concentration in the PEG-rich phase (bar 332), a yield of 45% was reached within 10 minutes of the extraction. The same yield of 45% could be reached in 15 minutes when the pDNA concentration in the PEG-rich phase was 100 ng/µl instead. With 100 ng/µl initial pDNA concentration in the PEG-rich phase (bar 331), a yield of 35% was reached within 10 minutes of the extraction. The extraction yield was found to be proportional to the initial pDNA concentration. This observation can be explained in terms of the concentration gradient. When the concentration gradient between the two liquid phases is high, the extraction yield (or rate) is higher. Thus, this study shows that when the initial concentration can be estimated, then the extraction time can be optimized accordingly.

EWOD Capability of Screening Liquid-Liquid Systems for DNA Extraction

Two-phase liquid system conditions often need to be optimized to achieve efficient extraction yield. The condition variables such as the type of the liquid-liquid system (such as ATPS, Aq./IL, phenol extraction, etc.), pH, temperature, and polymer/salt concentration can change the extraction efficiency. Typically, the system can be optimized on the final extraction yield from the process. Such optimization is a tedious process that requires substantial resources, including time and effort. An EWOD DMF technology is particularly useful to address this issue; an EWOD device can readily provide arrays of droplets, and each droplet carries unique ATPS formation conditions while they are individually controlled. These features make an EWOD device suitable for a high-throughput screening platform in which several liquid-liquid systems and variables can be tested.

Figure 34:
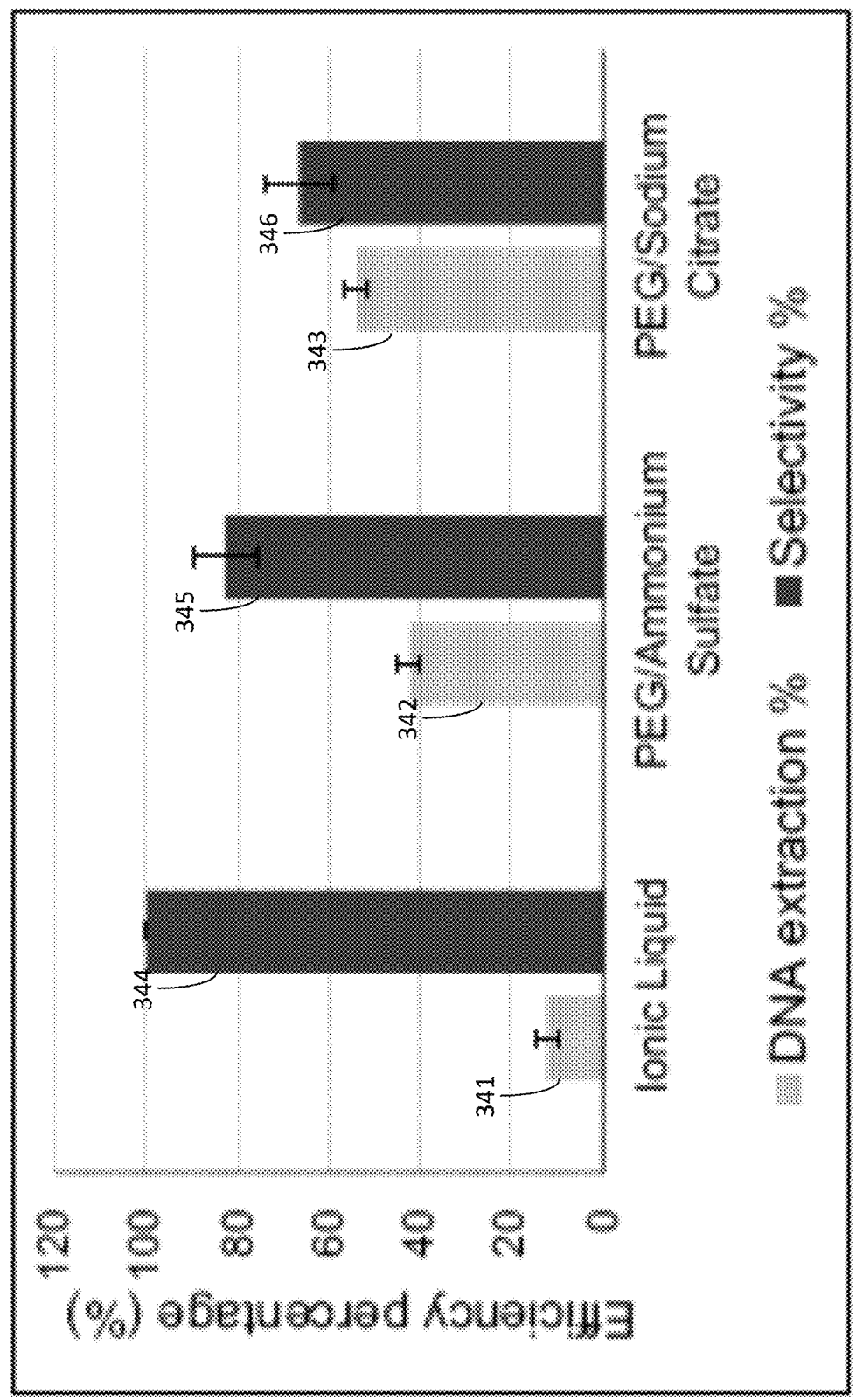
FIG. 34 is a bar graph of efficiency percentage plotted against DNA extraction and selectivity for different liquid-liquid systems, namely, IL, PEG/AS and PEG/SC.

As a demonstration of this capability of EWOD microfluidics, three different liquid-liquid systems were used in this entire work to study pDNA extraction in a DTD format on EWOD. The performance of the three systems studied is plotted in FIG. 34. FIG. 34 is a bar graph of efficiency percentage plotted against DNA extraction and selectivity for the different liquid-liquid systems, namely, IL, PEG/AS and PEG/SC. The bars 341-343 for each system represent the DNA extraction efficiency, and the bars 344-346 for each system represent the selectivity percentage for extraction experiments conducted for 15 minutes. The extraction with the Aq./IL system had minimal pDNA extraction. However, with protein molecules spiked in, no protein co-extraction was observed, making the pDNA selectivity to be maximum with the Aq./IL system, leading to a very pure pDNA in the extractant. The results from the two ATPS show higher pDNA extraction compared to IL, but with also some protein co-extraction. From FIG. 34, it can be concluded that the PEG/AS has a better compromise of both with DNA extraction as high as 45% and selectivity as high as 80% as attained on the EWOD platform.

This EWOD platform can be used to study several such liquid-liquid systems with varying parameters that make it very suitable for screening a library of systems. In this study, it has been shown that by changing the salt in the ATPS, different DNA extraction yield, and purity of the final sample can be achieved. Similarly, several other ILs can also be screened for higher extraction, besides the one studied here.

Conclusions of the Third Study

ATPE of DNA was demonstrated in the EWOD DMF platform for the first time. DNA was successfully isolated in the salt-rich phase using this platform. The procedures of extraction and separation require only a few minutes, and thus, this process is much faster than the traditional beaker aqueous two-phase extraction, which takes a few hours. The aqueous nature of the extractant makes the DNA extracted readily available for the next analysis in the workflow.

The idea behind this study has been twofold. The initial study was to demonstrate the successful transfer of pDNA from the PEG-rich phase to the salt-rich phase in a DTD format on EWOD microfluidics without the presence of any other impurities. The extraction by the two ATPSs obtained on-chip was compared, and it was found that the PEG/SC system showed a higher extraction yield. The second study consisted of spiking protein molecules in the PEG-rich phase, along with pDNA, and on-chip ATPE was studied for the two systems. The motivation of this study was to show the on-chip selective extraction of pDNA using the two ATPSs. PEG/SC system showed higher pDNA extraction; however, the protein co-extraction with the PEG/SC system was also significant. The conclusion can be made that the PEG/AS system is the best system for pDNA isolation and purification on-chip in the experimental conditions studied here, as it was able to eliminate the majority of the protein impurity and selectively extract pDNA molecules.

Due to the versatile nature of the device, the ATPS can be formed on the device for future studies. Further, different liquid-liquid systems and conditions can be quickly tested on-chip for rapid screening of their extraction performance. Parameters like different salt concentrations, salt combinations, pH, etc., can be rapidly tested in this platform. Overall, it is a more convenient, efficient, and effective method of studying different liquid-liquid systems as opposed to conducting experiments in lab-scale protocols.

It should be emphasized that the above-described embodiments of the present invention, particularly, any "preferred" or "representative" embodiments, are merely examples of implementations, set forth to provide a clear understanding of the inventive concepts and principles. Many variations and modifications may be made to the above-described embodiments without departing substantially from the inventive principles and concepts. All such modifications and variations are intended to be included herein within the scope of this disclosure.

For example, while the inventive principles and concepts have been described herein with reference to the EWOD device 20 and the system 100 having particular configurations, they may have other configurations, as will be understood by those of skill in the art in view of the description provided herein. Likewise, while the inventive principles and concepts have been described herein with reference to the methods having particular steps, they may be modified to have different steps, fewer steps or additional steps, as will be understood by those of skill in the art in view of the description provided herein.

What is claimed is:

1. A method for extracting biomolecules comprising:
   using liquid-to-liquid extraction (LLE) in an electrowetting on dielectric (EWOD) device to extract a particular type of biomolecules from a liquid one droplet that contains the particular type of biomolecules into a liquid two droplet and to separate the liquid two droplet having the particular type of biomolecules therein from the liquid one droplet to complete at least one cycle of LLE,
   wherein the process of using LLE in the EWOD device to extract the particular type of biomolecules from the liquid one droplet and to separate the liquid two droplet having the particular type of biomolecules therein from the liquid one droplet comprises:
   dispensing the liquid one droplet containing the particular type of biomolecules to be extracted and a liquid two droplet from a reservoir of the EWOD device into a mixing and extraction section of the EWOD device;
   in the mixing and extraction section, receiving the liquid one droplet and the liquid two droplet and mixing the liquid one droplet and the liquid two droplet together in a predetermined manner to extract the particular type of biomolecules into the liquid two droplet; and
   in a separation section of the EWOD device, separating the liquid two droplet having the particular type of biomolecules therein from the liquid one droplet to complete at least cycle of LLE.

2. The method of claim 1, wherein liquid two is an ionic liquid (IL).

3. The method of claim 2, further comprising:
   in a concentration measurement system of the EWOD device, analyzing the liquid two droplet after separation from the liquid one droplet and generating a concentration measurement signal indicative of a concentration of the particular type of biomolecules in the separated liquid two droplet.

4. The method of claim 3, wherein the concentration measurement system comprises:
   at least a first light source that generates light of a predetermined wavelength or wavelength range;
   at least a first optical detector that detects light passing through the separated liquid two droplet and generates the concentration measurement signal.

5. The method of claim 1, wherein the particular type of biomolecules is DNA.

6. The method of claim 1, wherein the particular type of biomolecules is RNA.

7. The method of claim 1, wherein the particular type of biomolecules is a protein.

8. The method of claim 1, wherein the liquid one and liquid two droplets comprise an aqueous two-phase system (ATPS), the liquid one droplet comprising an aqueous solution of polymer containing biomolecules and the liquid two droplet comprising one of an aqueous solution of polymer and an aqueous solution of salt the LLE being aqueous two-phase extraction (ATPE).

* * * * *